(12) United States Patent
Hong et al.

(10) Patent No.: US 11,306,073 B2
(45) Date of Patent: Apr. 19, 2022

(54) N-ACYLUREA DERIVATIVE AND COMPOSITION COMPRISING SAME FOR PREVENTION OR TREATMENT OF CARDIOVASCULAR DISEASE

(71) Applicants: KOREA UNIVERSITY RESEARCH AND BUSINESS FOUNDATION, Seoul (KR); KYUNGPOOK NATIONAL UNIVERSITY INDUSTRY-ACADEMIC COOPERATION FOUNDATION, Daegu (KR)

(72) Inventors: Soon Jun Hong, Seoul (KR); Chung Ho Kim, Gyeonggi-do (KR); Hyung Joon Joo, Seoul (KR); Jong-Ho Kim, Seoul (KR); Ji-Young Park, Seoul (KR); Seung Cheol Choi, Seoul (KR); Chan-Sik Yang, Seoul (KR); Jong Hwa Jung, Daegu (KR); Minseon Jeong, Gyeongsangbuk-do (KR); Miseon Ryu, Gyeongsangnam-do (KR); Sugyeong Kwon, Daegu (KR)

(73) Assignees: KOREA UNIVERSITY RESEARCH AND BUSINESS FOUNDATION, Daegu (KR); KYUNGPOOK NATIONAL UNIVERSITY INDUSTRY-ACADEMIC COOPERTION FOUNDATION, Daegu (KR)

(*) Notice: Subject to any disclaimer, the term of this patent is extended or adjusted under 35 U.S.C. 154(b) by 0 days.

(21) Appl. No.: 16/094,826

(22) PCT Filed: Dec. 22, 2016

(86) PCT No.: PCT/KR2016/015122
§ 371 (c)(1),
(2) Date: Oct. 18, 2018

(87) PCT Pub. No.: WO2017/188551
PCT Pub. Date: Nov. 2, 2017

(65) Prior Publication Data
US 2019/0119261 A1    Apr. 25, 2019

(30) Foreign Application Priority Data

Apr. 26, 2016   (KR) .................. 10-2016-0050817

(51) Int. Cl.
| *A61P 9/10* | (2006.01) |
| *A61P 9/12* | (2006.01) |
| *C07C 275/30* | (2006.01) |
| *C07C 275/50* | (2006.01) |
| *C07D 209/08* | (2006.01) |

(Continued)

(52) U.S. Cl.
CPC .......... *C07D 405/12* (2013.01); *A61K 9/0019* (2013.01); *A61K 9/145* (2013.01); *A61K 9/2018* (2013.01); *A61K 9/4866* (2013.01); *A61K 47/02* (2013.01); *C07C 275/30* (2013.01); *C07C 275/50* (2013.01); *C07D 209/08* (2013.01); *C07D 209/14* (2013.01); *C07D 213/61* (2013.01); *C07D 213/75* (2013.01); *C07D 257/04* (2013.01); *C07D 265/30* (2013.01); *C07D 295/10* (2013.01); *C07D 295/104* (2013.01); *C07D 295/185* (2013.01);

(Continued)

(58) Field of Classification Search
CPC ........................ C07D 405/12; C07D 295/185; C07D 403/12; C07D 295/104; C07D 209/14; C07D 213/75; C07D 209/08; C07D 213/61; C07D 265/30; C07D 295/10; C07D 317/64; C07D 257/04; C07C 275/50; C07C 275/30; A61K 9/2018; A61K 47/02; A61K 9/145; A61K 9/4866; A61K 9/0019; A61P 9/10; A61P 9/12; A61P 9/06; A61P 9/00
See application file for complete search history.

(56) References Cited

U.S. PATENT DOCUMENTS

| 4,103,018 A | 7/1978 | Neustadt et al. |
| 4,252,804 A | 2/1981 | Joullie et al. |
| 2007/0238672 A1 | 10/2007 | Dittrich et al. |

FOREIGN PATENT DOCUMENTS

| CA | 1125170 A | 6/1982 |
| CN | 102573486 A | 7/2012 |

(Continued)

OTHER PUBLICATIONS

Chemical Abstract Registry No. 880431-59-4, indexed in the Registry File on STN CAS Online Apr. 14, 2006.*

(Continued)

*Primary Examiner* — Amanda L. Aguirre
(74) *Attorney, Agent, or Firm* — Hultquist, PLLC; Steven J. Hultquist

(57) ABSTRACT

The present invention relates to a novel N-acylurea derivative and the use thereof for the prevention or treatment of cardiovascular disease, and more particularly to a novel N-acylurea derivative, a pharmaceutical composition for prevention or treatment of cardiovascular disease, which contains the N-acylurea derivative as an active ingredient, and a method of preparing the N-acylurea derivative. The N-acylurea derivative according to the present invention can inhibit platelet aggregation by inhibiting the activity of talin in the intracellular matrix, and thus can be useful for the prevention or treatment of cardiovascular disease.

8 Claims, 7 Drawing Sheets
(4 of 7 Drawing Sheet(s) Filed in Color)

(51) Int. Cl.

| | |
|---|---|
| C07D 209/14 | (2006.01) |
| C07D 213/61 | (2006.01) |
| C07D 213/75 | (2006.01) |
| C07D 257/04 | (2006.01) |
| C07D 265/30 | (2006.01) |
| C07D 295/10 | (2006.01) |
| C07D 295/104 | (2006.01) |
| C07D 295/185 | (2006.01) |
| C07D 317/64 | (2006.01) |
| C07D 403/12 | (2006.01) |
| C07D 405/12 | (2006.01) |
| A61K 47/02 | (2006.01) |
| A61K 9/00 | (2006.01) |
| A61K 9/14 | (2006.01) |
| A61K 9/20 | (2006.01) |
| A61K 9/48 | (2006.01) |

(52) U.S. Cl.
CPC ......... *C07D 317/64* (2013.01); *C07D 403/12* (2013.01); *A61P 9/10* (2018.01); *A61P 9/12* (2018.01)

(56) References Cited

FOREIGN PATENT DOCUMENTS

| | | |
|---|---|---|
| EP | 0007648 A1 | 2/1980 |
| JP | S53135945 A | 11/1978 |
| JP | S55113770 U | 9/1980 |
| JP | S5659755 A | 5/1981 |
| JP | S5982374 A | 5/1984 |
| JP | 2009532479 A | 9/2009 |
| JP | 2012529512 A | 11/2012 |
| WO | WO2004106292 A1 | 12/2004 |
| WO | WO2007115410 A1 | 10/2007 |
| WO | WO2008089152 A2 | 7/2008 |
| WO | WO2009137681 A1 | 11/2009 |
| WO | 2010144345 A1 | 12/2010 |
| WO | WO2012047017 A2 | 4/2012 |
| WO | WO2014145028 A2 | 9/2014 |
| WO | WO2014145029 A2 | 9/2014 |
| WO | WO2015006181 A1 | 1/2015 |
| WO | WO2015035051 A1 | 3/2015 |

OTHER PUBLICATIONS

Chemical Abstract Registry No. 790681-56-0, indexed in the Registry File on STN CAS Online Nov. 30, 2004.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Ito et al., A medium-term rat liver bioassay for rapid in vivo detection of carcinogenic potential of chemicals. Cancer Science, 2003, 94, 1, 3-8.*
PubChem SID 115550736, NIH PubChem Database (online), U.S. National Library of Medicine [Available: Mar. 28, 2011], (Year: 2011).*
Registry No. 13909-96-1, STN Database (online), Chemical Abstract Service [Entered STN: Nov. 16, 1984], (Year: 1984).*
Registry No. 5205-56-1, STN Database (online), Chemical Abstract Service [Entered STN: Nov. 16, 1984], (Year: 1984).*
Registry No. 5205-55-0, STN Database (online), Chemical Abstract Service [Entered STN: Nov. 16, 1984], (Year: 1984).*
Registry No. 5205-54-9, STN Database (online), Chemical Abstract Service [Entered STN: Nov. 16, 1984], (Year: 1984).*
CAS STN Registry No. 1003819-55-3 [Entered STN: Feb. 17, 2008], (Year: 2008).*
PubChem Identifier CID 36096763 (Create Date: May 29, 2009). (Year: 2009).*
STN Registry No. 1016398-50-7 Entry [Entered STN: Apr. 22, 2008], (Year: 2008).*
PubChem Identifier CID 8932071 (Create Date: Jul. 30, 2006). (Year: 2006).*
Chemical Abstract Service STN Registry Database, Registry No. 4791-10-1 [Entered STN: Nov. 16, 1984], (Year: 1984).*
Chemical Abstract Service STN Registry Database, Registry No. 82004-99-7 [Entered STN: Nov. 16, 1984], (Year: 1984).*
Chemical Abstract Service, STN Database, Registry Nos. 24217-26-3 [Entered STN: Nov. 16, 1984], (Year: 1984).*
Claims 1-2, 4 and 6-7 are rejected under 35 U.S.C. 102(a)(1) as being anticipated by Chemical Abstract Service, STN Database, Registry No. 29653-94-9 [Entered STN: Nov. 16, 1984], (Year: 1984).*
Chemical Abstract Service, STN Database, Registry Nos. 24217-27-4 [Entered STN: Nov. 16, 1984], (Year: 1984).*
Chemical Abstract Service, STN Database, Registry No. 39764-03-9 [Entered STN: Nov. 16, 1984], (Year: 1984).*
Chemical Abstract Service, STN Database, Registry No. 21396-91-8 [Entered STN: Nov. 16, 1984], (Year: 1984).*
Chemical Abstract Service, STN Database, Registry No. 1289443-36-2 [Entered STN: May 3, 2011], (Year: 2011).*
Registry No. 1002699-55-9, Chemical Abstract Service, STNext Database (online) [Entered STN: Feb. 11, 2008], (Year: 2008).*
Registry No. 903790-85-2, Chemical Abstract Service, STNext Database (online) [Entered STN: Aug. 23, 2006], (Year: 2006).*
Registry No. 878417-88-0, Chemical Abstract Service, STNext Database (online) [Entered STN: Mar. 29, 2006], (Year: 2006).*
Registry No. 1003819-52-0, Chemical Abstract Service, STNext Database (online) [Entered STN: Feb. 17, 2008], (Year: 2008).*
Registry No. 938553-98-1, Chemical Abstract Service, STNext Database (online) [Entered STN: Jun. 24, 2007], (Year: 2007).*
Registry No. 1388382-18-0, Chemical Abstract Service, STNext Database (online) [Entered STN: Aug. 9, 2012], (Year: 2012).*
Registry No. 938628-86-5, Chemical Abstract Service, STNext Database (online) [Entered STN: Jun. 24, 2007], (Year: 2007).*
Registry No. 1252455-53-0, Chemical Abstract Service, STNext Database (online) [Entered STN: Nov. 10, 2010], (Year: 2010).*
Liu, C., et al., "Novel Hybrid Virtual Screening Protocol Based on Molecular Docking and Structure-Based Pharmacophore for Discovery of Methionyl-tRNA Synthetase Inhibitors as Antibacterial Agents", "Int. J. Mol. Sci.", 2013, pp. 14225-14239, vol. 14.
Monkley, S., et al., "Disruption of the Talin Gene Arrests Mouse Development at the Gastrulation Stage", "Developmental Dynamics", 2000, pp. 560-574, vol. 219.
Nieswandt, B., et al., "Loss of Talin1 in Platelets Abrogates Integrin Activation, Platelet Aggregation, and Thrombus Formation In Vitro and In Vivo", "The Journal of Experimental Medicine", 2007, pp. 3113-3118, vol. 204, No. 13.
Petrich, B., et al., "Talin is Required for Integrin-Mediated Platelet Function in Hemostasis and Thrombosis", "The Journal of Experimental Medicine", 2007, pp. 3103-3111, vol. 204, No. 13.
STN, "STN Registry Database Results", "STN Registry", Apr. 14, 2006, pp. 1-4.
Michelson, Alan D., "Platelets, Second Edition", 2007, Publisher: Elsevier.
Deeb, O., et al., "QSAR of Novel Hydroxyphenylureas as Antioxidant Agents", "QSAR Comb. Sci.", 2008, pp. 417-424, No. 4.
Fortin, S., et al., "Synthesis, Antiproliferative Activity Evaluation and Structure-Activity Relationships of Novel Aromatic Urea and Amide Analogues of N-Phenyl-N'-(2-Chloroethyl)Ureas", "Eur. J. Med. Chem.", 2010, pp. 2928-2937, vol. 45, No. 7.
Kishore, V., et al., "Synthesis of 2,5 Disubstituted Tetrazoles as Possible Antiinflammatory Agents", "J. Heterocycl. Chem.", 1978, pp. 1335-1338, vol. 15.
Parma, S.S., et al., "Substituted Carbamides: Interrelationship Between Anticonvulsant Activity and Inhibition of Nicotinamide Adenine Dinucleotide-Dependent Pyruvic Acid Oxidation", "Journal of Pharmaceutical Sciences", 1972, pp. 1366-1338, vol. 61, No. 9.

(56) References Cited

OTHER PUBLICATIONS

Shao, K., et al., "Synthesis and Antitumor Activity Evaluation of Pyrimidine Analogues Bearing Urea Moiety", "Chinese J. Chem", 2014, pp. 443-447, vol. 32.
Verderame, M., "1,4-Disubstituted Piperazines 3. Piperazinylbenzothiazoles", "J. Med. Chem.", 1972, pp. 693-694, vol. 15, No. 6.
Verma, S., et al., "Synthesis of Phenylurea Derivatives and Their Evaluation as Antihyperglycaemic Agents", "Indo Global Journal of Pharmaceutical Sciences", 2013, pp. 33-39, vol. 3, No. 1.

* cited by examiner

N-ACYLUREA DERIVATIVE AND COMPOSITION COMPRISING SAME FOR PREVENTION OR TREATMENT OF CARDIOVASCULAR DISEASE

CROSS-REFERENCE TO RELATED APPLICATIONS

This application is a U.S. national phase under the provisions of 35 U.S.C. § 371 of International Patent Application No. PCT/KR16/15122 filed Dec. 22, 2016, which in turn claims priority of Korean Patent Application No. 10-2016-0050817 filed Apr. 26, 2016.

The applicants acknowledge the financial support of the following grants involving work related to the present disclosure: (1) the research program entitled "Preclinical Development of Novel Antiplatelet Drugs Using Integrin-Talin Signaling Pathway" was supported by a grant of the Korea Health Technology R&D Project through the Korea Health Industry Development Institute (KHIDI), funded by the Ministry of Health & Welfare, Republic of Korea (Project grant number: HI14CO209), and managed by KOREA UNIVERSITY RESEARCH AND BUSINESS FOUNDATION from Jun. 1, 2014 to May 31, 2018; and (2) the research program entitled "Novel anti-platelet agent development and efficacy verification targeting new mechanism of Glycoprotein IIb/IIIa inside-out signaling" was supported by the Bio & Medical Technology Development Program of the National Research Foundation (NRF), funded by the Ministry of Science & ICT (Project grant number: NRF-2018M3A9A8017949), and managed by KOREA UNIVERSITY RESEARCH AND BUSINESS FOUNDATION from Apr. 1, 2018 to Dec. 31, 2019.

TECHNICAL FIELD

The present invention relates to a novel N-acylurea derivative and the use thereof for the prevention or treatment of cardiovascular disease, and more particularly to a novel N-acylurea derivative, a pharmaceutical composition for preventing or treating cardiovascular disease, which contains the N-acylurea derivative as an active ingredient, and a method of preparing the N-acylurea derivative.

BACKGROUND ART

Talin molecule which is one of the cytoskeletal components is a cytoplasmic protein. It is known that the talin molecule links integrin to the cytoskeleton directly or indirectly by interaction with vinculin and α-actinin (Alan D. Michelson, Platelets, Second Edition, 2006).

In the report on abnormalities in the talin molecule network, it was reported that the knockout of the talin molecule makes it impossible to develop into a normal individual after fertilization and leads to death within 8 days after fertilization, indicating that the talin molecule is a developmentally important molecule (Dev Dyn., 219:560, 2000).

Studies on the relationship between talin molecules and platelets indicated that the activities of integrin and talin molecules play an important role in the adhesion and aggregation of platelets. Adhesion and aggregation of platelets occur due to vascular endothelial wound, and the activation of integrin by talin molecules occurs. On the contrary, it is known that talin-deficient platelets do not induce activation of integrin, and thus reduce thrombosis (J Exp. Med., 204(13):3113, 2007). In addition, it was reported that the knockout of talin molecules in megakaryocytes which are platelet precursors results in inhibition of talin-induced integrin activation, causing continuous hemorrhage (J Exp. Med, 204(13):3103, 2007). Therefore, the regulation of talin molecule activity can lead to the inhibition of platelet aggregation and the reduction of thrombosis and bleeding.

Accordingly, the present inventors have made extensive efforts to develop a substance capable of treating and preventing talin-related diseases by reducing talin expression, and as a result, have synthesized novel N-acylurea derivatives and have found that the novel N-acylurea derivatives exhibit the effect of inhibiting platelet aggregation by inhibiting the activity of talin and effectively regulating cellular morphological changes and growth, thereby completing the present invention.

SUMMARY OF THE INVENTION

It is an object of the present invention to provide a novel N-acylurea derivative or a pharmaceutically acceptable salt thereof.

Another object of the present invention is to provide a pharmaceutical composition for the prevention or treatment of cardiovascular disease, comprising the N-acyl urea derivative or the pharmaceutically acceptable salt thereof as an active ingredient.

Still another object of the present invention is to provide a method of preparing the N-acylurea derivative or the pharmaceutically acceptable salt thereof.

To achieve the above objects, the present invention provides a novel N-acylurea derivative which is a compound represented by Formula 1 below, or a pharmaceutically acceptable salt thereof:

[Formula 1]

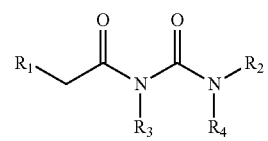

wherein $R_1$ is hydrogen, halogen, hydroxy, $C_{1-6}$ alkyl, $C_{1-6}$ haloalkyl, $C_{6-12}$ aryl, $C_{1-12}$ heteroaryl, $C_{1-12}$ heterocyclyl, $C_{1-6}$ alkyl linked by heteroatom, or a $C_{6-12}$ aryl linked by heteroatom, $C_{1-12}$ heteroaryl or $C_{1-12}$ heterocyclyl, wherein the aryl, heteroaryl or heterocyclyl may be unsubstituted or substituted, and the heteroatom is selected from N, O and S;

$R_2$ is hydrogen, $C_{1-6}$ alkyl, $C_{1-6}$ haloalkyl, $C_{6-12}$ aryl, $C_{1-12}$ heteroaryl, $C_{1-12}$ heterocyclyl, $C_{2-20}$ alkylene-$C_{6-12}$ aryl, $C_{2-20}$ alkylene-$C_{1-12}$ heteroaryl, or $C_{2-20}$ alkylene-$C_{1-12}$ heterocyclyl, wherein the aryl, heteroaryl or heterocyclyl may be unsubstituted or substituted, and the heteroatom is selected from N, O and S; and $R_3$ and $R_4$ are each independently hydrogen, $C_{1-6}$ alkyl or $C_{1-6}$ haloalkyl.

The present invention also provides a pharmaceutical composition for the prevention or treatment of cardiovascular disease, which contains the novel N-acylurea derivative or the pharmaceutically acceptable salt thereof as an active ingredient.

The present invention also provides a method of preparing the novel N-acyl urea derivative represented by above Formula 1, or the pharmaceutically acceptable salt thereof, comprising: (a) obtaining acetamide by mixing and reacting 2-chloroacetamide, N,N-dimethylformamide, potassium carbonate and a nucleophilic reagent in a reactor, terminating a reaction by addition of water, followed by concentrating; (b) obtaining acetyl isocyanate by adding oxalyl chloride to the obtained acetamide, adding dichloroethane and heating and stirring, followed by concentrating; and (c) obtaining a compound by adding methylene chloride to the obtained acetyl isocyanate, adding and reacting a nucleophilic reagent, followed by concentrating.

The present invention also provides a method of preparing the N-acyl urea derivative of above Formula 1, or the pharmaceutically acceptable salt thereof, comprising: (a) obtaining 2-chloroacetyl isocyanate by mixing 2-chloroacetamide and oxalyl chloride in a reactor, adding dichloroethane and heating and stirring, followed by concentrating; (b) obtaining carbamoyl 2-chloroacetamide by adding methylene chloride to the obtained 2-chloroacetyl isocyanate, and then adding a nucleophilic reagent and reacting, followed by concentrating; and (c) obtaining N-acylurea derivative by adding methanol to the obtained carbamoyl 2-chloroacetamide, adding and reacting a nucleophilic reagent while stirring, extracting an N-acylurea derivative using an organic solvent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a schematic view showing an experimental method for high-throughput screening of thrombosis inhibitory candidates in Example 38 of the present invention.

In FIG. 2, 0% is a negative control and represents the degree to which cells adhere to a surface coated with bovine serum albumin (BSA) instead of fibrinogen, and 100% is a positive control and represents the degree to which cells adhere to fibrinogen in the absence of any candidate. The ability of candidates to inhibit fibrinogen binding was normalized to 100%, and the mean and standard error of three experiments are graphically shown.

BEST MODE FOR CARRYING OUT THE INVENTION

Figure 1:
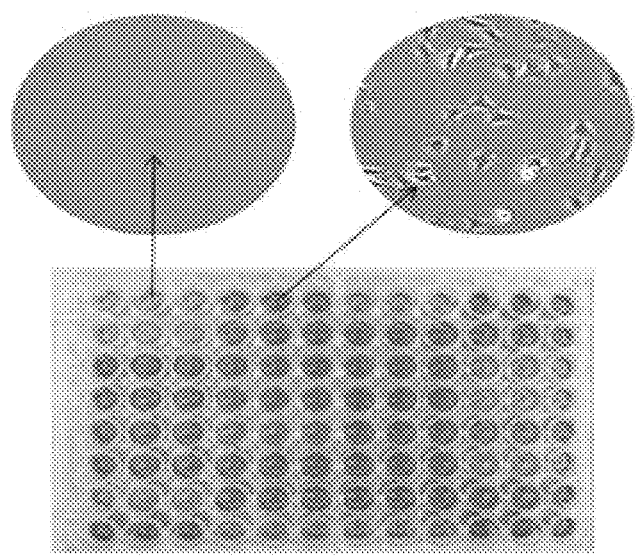
FIG. 1 shows the results of Western blot analysis performed to confirm the effect of a compound of the present invention (a compound of Preparation Example 30 or a compound of Preparation Example 31) on the inhibition of β-catenin expression in HEK293 cells in which the Wnt/β-catenin pathway was activated by treatment with Wnt-3a CM.

In one aspect, the present invention is directed to an N-acylurea derivative represented by Formula 1 below or a pharmaceutically acceptable salt thereof:

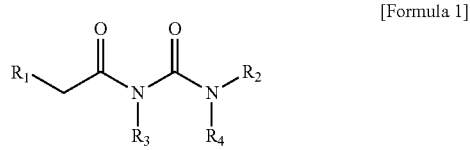

[Formula 1]

wherein $R_1$ is hydrogen, halogen, hydroxy, $C_{1-6}$ alkyl, $C_{1-6}$ haloalkyl, $C_{6-12}$ aryl, $C_{1-12}$ heteroaryl, $C_{1-12}$ heterocyclyl, $C_{1-6}$ alkyl linked by heteroatom, or a $C_{6-12}$ aryl linked by heteroatom, $C_{1-12}$ heteroaryl or $C_{1-12}$ heterocyclyl, wherein the aryl, heteroaryl or heterocyclyl may be unsubstituted or substituted, and the heteroatom is selected from N, O and S;

$R_2$ is hydrogen, $C_{1-6}$ alkyl, $C_{1-6}$ haloalkyl, $C_{6-12}$ aryl, $C_{1-12}$ heteroaryl, $C_{1-12}$ heterocyclyl, $C_{2-20}$ alkylene-$C_{6-12}$ aryl, $C_{2-20}$ alkylene-$C_{1-12}$ heteroaryl, or $C_{2-20}$ alkylene-$C_{1-12}$ heterocyclyl, wherein the aryl, heteroaryl or heterocyclyl may be unsubstituted or substituted, and the heteroatom is selected from N, O and S; and $R_3$ and $R_4$ are each independently hydrogen, $C_{1-6}$ alkyl or $C_{1-6}$ haloalkyl.

As used herein, the term "$C_{1-6}$ alkyl" refers to a monovalent linear or branched saturated hydrocarbon radical (or moiety), consisting solely of carbon and hydrogen atoms, having one to six carbon atoms. Examples of alkyl groups include, but are not limited to, methyl, ethyl, propyl, isopropyl, butyl, isobutyl, sec-butyl, tert-butyl, pentyl, n-hexyl and the like. Examples of "branched alkyl" include isopropyl, isobutyl, tert-butyl and the like.

The term "$C_{1-6}$ haloalkyl" means a $C_{1-6}$ alkyl as defined herein wherein at least one of the hydrogen atoms of the alkyl group has been substituted by the same or different halogen atoms. Examples of haloalkyl include —$CH_2Cl$, —$CH_2CF_3$, —$CH_2CCl_3$, perfluoroalkyl (e.g., —$CF_3$) and the like.

The term "$C_{2-20}$ alkylene" means a linear saturated divalent hydrocarbon radical having 2 to 20 carbon atoms, or a branched saturated divalent hydrocarbon radical having 3 to 20 carbon atoms, e.g., methylene, ethylene, 2,2-dimethylethylene, propylene, 2-methylpropylene, butylene, pentylene, and the like.

The term "$C_{1-6}$ alkoxy" means to a moiety of the formula —O—$C_{1-6}$ alkyl. Examples of $C_{1-6}$ alkoxy moieties include, but are not limited to, methoxy, ethoxy, isopropoxy, tert-butoxy, and the like.

The term "$C_{6-12}$ aryl" means a monovalent cyclic aromatic hydrocarbon radical having 6 to 12 carbon atoms and consisting of a mono-, bi- or tricyclic aromatic ring. The aryl group may be substituted or unsubstituted as defined herein. In one embodiment, the aryl group may be a substituted or unsubstituted phenyl group, or a substituted or unsubstituted naphthyl group. In particular, in one embodiment, the aryl group is a substituted or unsubstituted phenyl group.

The term "$C_{1-12}$ heteroaryl" means a monocyclic, bicyclic or tricyclic radical of 5 to 12, specifically 6 to 10 ring atoms having at least one aromatic ring containing one, two, or three ring heteroatoms selected from N, O, and S, the remaining ring atoms being C, with the understanding that the attachment point of the heteroaryl radical will be on an aromatic ring. The heteroaryl ring may be a 5- or 6-membered monocyclic ring containing one, two, or three ring heteroatoms selected from N, O and S, the remaining ring atoms being C. The heteroaryl ring may be substituted or unsubstituted as defined herein. Examples of heteroaryl moieties include, but are not limited to, pyrrolyl, imidazolyl, pyrazolyl, triazolyl, tetrazolyl, oxazolyl, isoxazolyl, thiazolyl, isothiazolyl, oxadiazolyl, thiadiazolyl, thienyl (i.e., thiopenyl), furanyl, pyranyl, pyridinyl, pyrimidinyl, pyrazinyl, pyridazinyl, quinolinyl, iso quinolinyl, benzofuryl (i.e., benzofuranyl), benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl, and the like, which may be each substituted or unsubstitued. Examples of preferable heteroaryl moieties includes pyrrolyl, imidazolyl, pyrazolyl, triazolyl, tetrazolyl, indolyl, pyridinyl, pyrimidinyl, pyrazinyl, and pyridazinyl, which may be each substituted or unsubstitued. In one embodiment, the heteroaryl moiety is triazolyl, tetrazolyl, pyridinyl, or indolyl, which may be each substituted or unsubstitued as defined herein.

The term "$C_{1-12}$ heterocyclyl" means a 4- to 9-membered saturated or partially unsaturated carbocyclic ring containing, in addition to carbon atoms, one, two, or three ring heteroatoms selected from N, O and S. Here, the two rings share two common ring atoms. That is, the bridge that separates the two rings is a single bond or a 1- or 2-membered chain. The heterocyclyl ring may be substituted or unsubstituted as defined herein. Examples of heterocyclyl moieties include, but are not limited to, azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, piperazinyl, morpholinyl, thiomorpholinyl, 1,1-dioxo-thiomorpholin-4-yl, azepanyl, diazepanyl, homopiperazinyl, oxazepanyl, dihydroindolyl, dihydrofuryl, dihydroimidazolinyl, dihydrooxazolyl, tetrahydropyridinyl, dihydropyranyl, or benzodioxolyl. In one embodiment, heterocyclyl is piperazinyl, morpholinyl, benzodioxolyl, or dihydroindolyl, which may be each substituted or unsubstitued as defined herein.

The term "aryl, heteroaryl or heterocyclyl linked by heteroatom" refers to aryl, heteroaryl or heterocyclyl linked by the heteroatom O, S or Se. In one embodiment, the heteroatom is O or S.

In the above Formula 1, $R_1$ is hydrogen, halogen, hydroxy, $C_{1-6}$ alkyl, $C_{1-6}$ haloaklyl, $C_{6-12}$ aryl, $C_{1-12}$ heteroaryl, $C_{1-12}$ heterocyclyl, $C_{1-6}$ alkyl linked by heteroatom, or a $C_{6-12}$ aryl linked by heteroatom, $C_{1-12}$ heteroaryl or $C_{1-12}$ heterocyclyl, wherein the aryl, heteroaryl or heterocyclyl may be unsubstituted or substituted with one to three substituents selected from the group consisting of halogen, hydroxy, $C_{1-6}$ alkyl, $C_{1-6}$ haloaklyl, $C_{1-6}$ alkoxy, $C_{1-6}$ haloalkoxy, —$C_{1-6}$ alkoxy-$C_{1-6}$ alkyl, $C_{1-6}$ alkoxycarbonyl, —O-aryl, —O-heteroaryl, and O—$C_{2-20}$ alkylene-aryl.

In one embodiment, $R_1$ is tetrazolyl, piperazinyl, morpholinyl, phenyl linked by O, or benzodioxolyl linked by O, wherein the tetrazolyl, piperazinyl, morpholinyl or benzodioxolyl may be unsubstituted or substituted with 1 to 3 substituents selected from the group consisting of halogen, $C_{1-6}$ haloalkyl, $C_{1-6}$ alkoxy, $C_{1-6}$ alkoxycarbonyl, phenoxy, and —O—$C_{2-20}$ alkylene-phenyl. Specifically, the tetrazolyl, piperazinyl, morpholinyl or benzodioxolyl may be substituted with 1 to 3 substituents selected from the group consisting of F, Br, $CF_3$, methoxy, t-butoxycarbonyl, phenoxy, and —O—$CH_2$-phenyl.

In Formula 1 above, $R_2$ is hydrogen, $C_{1-6}$ alkyl, $C_{1-6}$ haloalkyl, $C_{6-12}$ aryl, $C_{1-12}$ heteroaryl, $C_{1-12}$ heterocyclyl, $C_{2-20}$ alkylene-$C_{6-12}$ aryl, $C_{2-20}$ alkylene-$C_{1-12}$ heteroaryl, or $C_{2-20}$ alkylene-$C_{1-12}$ heterocyclyl, wherein the aryl, heteroaryl or heterocyclyl may be unsubstituted or substituted with one to three substituents selected from the group consisting of halogen, hydroxy, $C_{1-6}$ alkyl, $C_{1-6}$ haloaklyl, $C_{1-6}$ alkoxy, $C_{1-6}$ haloalkoxy, —$C_{1-6}$ alkoxy-$C_{1-6}$ alkyl, $C_{1-6}$ alkoxycarbonyl, —O-aryl, —O-heteroaryl, and O—$C_{2-20}$ alkylene-$C_{6-12}$ aryl.

In one embodiment, $R_2$ is phenyl, pyridinyl, $C_{2-20}$ alkylene-phenyl, $C_{2-20}$ alkylene-indolyl, or $C_{2-20}$ alkylene-dihydroindolyl, wherein the phenyl, pyridinyl, indolyl, or dihydroindolyl may be unsubstituted or substituted with one to three substituents selected from the group consisting of halogen, hydroxy, $C_{1-6}$ alkyl, $C_{1-6}$ haloaklyl, $C_{1-6}$ alkoxy, $C_{1-6}$ haloalkoxy, —$C_{1-6}$ alkoxy-$C_{1-6}$ alkyl, —O-phenyl, and –O—$C_{2-20}$ alkylene-phenyl.

In one embodiment, $R_2$ is phenyl, pyridinyl, $C_{2-6}$ alkylene-phenyl, $C_{2-6}$ alkylene-indolyl, or $C_{2-6}$ alkylene-dihydroindolyl, wherein the phenyl, pyridinyl, indolyl, or dihydroindolyl may be unsubstituted or substituted with one to three substituents selected from the group consisting of halogen, $C_{1-6}$ alkoxy, phenoxy, and —O—$C_{2-6}$ alkylene-phenyl. Specifically, the phenyl, pyridinyl, indolyl, or dihydroindolyl may be substituted with 1 to 3 substituents selected from the group consisting of F, Br, methoxy, phenoxy, and —O—$CH_2$-phenyl.

In Formula 1 above, $R_3$ and $R_4$ are each independently hydrogen, $C_{1-6}$ alkyl, or $C_{1-6}$ haloalkyl.

In one embodiment, $R_3$ and $R_4$ are each hydrogen.

Specific examples of the novel N-acylurea derivative which is a compound represented by the formula 1 of the present invention include:

(1) N-((4-bromo-3-methoxyphenl)carbamoyl)-2-(5-phenyl-2H-tetrazol-2-yl)acetamide;
(2) N-((4-phenoxyphenyl)carbamoyl)-2-(5-phenyl-2H-tetrazol-2-yl)acetamide;
(3) N-((4-methoxybenzyl)carbamoyl)-2-(5-phenyl-2H-tetrazol-2-yl)acetamide;
(4) N-((2-(3a,7a-dihydro-1H-indol-3-yl)ethyl)carbamoyl)-2-(5-phenyl-2H-tetrazol-2-yl)acetamide);
(5) N-((2,4-dimethoxyphenyl)carbamoyl)-2-(5-phenyl-2H-tetrazol-2-yl)acetamide;
(6) N-((4-(benzyloxy)phenyl)carbamoyl)-2-(5-phenyl-2H-tetrazol-2-yl)acetamide;

(7) N-((2-fluorophenyl)carbamoyl)-2-(5-phenyl-2H-tetrazol-2-yl)acetamide;
(8) 2-(benzo[d][1,3]dioxol-5-yloxy)-N-((3-fluoropyridin-2-yl)carbamoyl)acetamide;
(9) 2-(benzo[d][1,3]dioxol-5-yloxy)-N-((4-bromo-3-methoxyphenyl)carbamoyl)acetamide;
(10) 2-(benzo[d][1,3]dioxol-5-yloxy)-N-((4-phenoxyphenyl)carbamoyl)acetamide;
(11) 2-(benzo[d][1,3]dioxol-5-yloxy)-N-((4-methoxybenzyl)carbamoyl)acetamide;
(12) N-((2-(1H-indol-3-yl)ethyl)carbamoyl)-2-(benzo[d][1,3]dioxol-5-yloxy)acetamide;
(13) 2-(benzo[d][1,3]dioxol-5-yloxy)-N-((2,4-dimethoxyphenyl)carbamoyl)acetamide;
(14) 2-(benzo[d][1,3]dioxol-5-yloxy)-N-((4-(benzyloxy)phenyl)carbamoyl)acetamide;
(15) 2-(benzo[d][1,3]dioxol-5-yloxy)-N-((2-fluorophenyl)carbamoyl)acetamide;
(16) N-((3-fluoropyridin-2-yl)carbamoyl)-2-(2-methoxyphenoxy)acetamide;
(17) N-((4-bromo-3-methoxyphenyl)carbamoyl)-2-(2-methoxyphenoxy)acetamide;
(18) 2-(2-methoxyphenoxy)-N-((4-phenoxyphenyl)carbamoyl)acetamide;
(19) N-((4-methoxybenzyl)carbamoyl)-2-(2-methoxyphenoxy)acetamide;
(20) N-((2-(1H-indol-3-yl)ethyl)carbamoyl)-2-(benzo[d][1,3]dioxol-5-yloxy)acetamide;
(21) N-((2,4-dimethoxyphenyl)carbamoyl)-2-(2-methoxyphenoxy)acetamide;
(22) N-((4-(benzyloxy)phenyl)carbamoyl)-2-(2-methoxyphenoxy)acetamide;
(23) N-((2-fluorophenyl)carbamoyl)-2-(2-methoxyphenoxy)acetamide;
(24) 2-(3,5-bis(trifluoromethyl)phenoxy)-N-((3-fluoropyridin-2-yl)carbamoyl)acetamide;
(25) 2-(3,5-bis(trifluoromethyl)phenoxy)-N-((4-bromo-3-methoxyphenyl)carbamoyl)acetamide;
(26) 2-(3,5-bis(trifluoromethyl)phenoxy)-N-((4-bromo-3-methoxyphenyl)carbamoyl)acetamide;
(27) 2-(3,5-bis(tri fluoromethyl)phenoxy)-N-((4-methoxybenzyl)carbamoyl)acetamide;
(28) N-((2-(1H-indol-3-yl)ethyl)carbamoyl)-2-(3,5-bis(trifluoromethyl)phenoxy)acetamide;
(29) 2-(3,5-bis(trifluoromethyl)phenoxy)-N-((2,4-dimethoxyphenyl)carbamoyl)acetamide;
(30) N-((4-(benzyloxy)phenyl)carbamoyl)-2-(3,5-bis(trifluoromethyl)phenoxy)acetamide;
(31) 2-(3,5-bis(trifluoromethyl)phenoxy)-N-((2-fluorophenyl)carbamoyl)acetamide;
(32) N-((4-bromo-3-methoxyphenyl)carbamoyl)-2-(3-bromophenoxy)acetamide;
(33) 2-(3-bromophenoxy)-N-((2,4-dimethoxyphenyl)carbamoyl)acetamide;
(34) 2-(2,3-dimethylphenoxy)-N-((2-fluorophenyl)carbamoyl)acetamide;
(35) 2-(4-(benzyloxy)phenoxy)-N-((2-fluorophenyl)carbamoyl)acetamide;
(36) N-((2-fluorophenyl)carbamoyl)-2-morpholinoacetamide; and
(37) tert-butyl 4-(2-(3-(2-fluorophenyl)ureido)-2-oxoethyl)piperazine-1-carboxylate.

The N-acylurea derivative of Formula 1 above according to the present invention comprises a pharmaceutically acceptable salt thereof, and a hydrate and a solvate prepared therefrom.

As used herein, the compound represented by Formula 1 designated is intended to embrace a pharmaceutically acceptable salt thereof. The pharmaceutically acceptable salt can be prepared by a salt preparation method that is commonly used in the art.

As used herein, the term "pharmaceutically acceptable salt" refers to a salt prepared from a pharmaceutically acceptable non-toxic base or acid including an inorganic or organic base and an inorganic or organic acid. The salt derived from an inorganic base is preferably aluminum, ammonium, calcium, magnesium, potassium or sodium salt. A solid salt may have one or more crystal structures, or otherwise may be in the form of a hydrate. Examples of the salt derived from a pharmaceutically acceptable non-toxic organic base include a primary, secondary or tertiary amine, a substituted amine such as a naturally-occurring substituted amine, a cyclic amine, or a basic ion exchange resin such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resin, procaine, purine, theobromine, triethylamine, trimethylamine, tripropylamine, tromethamine, or the like.

When the compound of the present invention is basic, a salt thereof may be prepared from pharmaceutically acceptable non-toxic acids including inorganic and organic acids. Examples of the acid include acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluene sulfonic acid, and the like. Particularly, the pharmaceutically acceptable salt may preferably be acetic, citric, hydrobromic, hydrochloric, maleic, phosphoric, sulfuric, fumaric, or tartaric acid.

A hydrate of a compound represented by Formula 1 of the present invention or a pharmaceutically acceptable salt thereof is intended to embrace a stoichiometric or non-stoichiometric amount of water bound thereto by non-covalent intermolecular forces. The hydrate may contain one or more equivalents of water, typically 1 to 5 equivalents of water. The hydrate may be prepared by crystallization of the compound represented by Formula 1 of the present invention or a pharmaceutically acceptable salt thereof in water or water-containing solvent.

A solvate of a compound represented by Formula 1 of the present invention or a pharmaceutically acceptable salt thereof is intended to embrace a stoichiometric or non-stoichiometric amount of a solvent bound thereto by non-covalent intermolecular forces. Preferred solvents are volatile, non-toxic, and suitable for administration to humans. In another aspect, the present invention is directed to a pharmaceutical composition for the prevention or treatment of cardiovascular disease, which contains a novel N-acylurea derivative or a pharmaceutically acceptable salt thereof as an active ingredient.

The cardiovascular disease of the present invention includes, but is not limited to, hypertension, ischemic heart disease, coronary artery disease, angina pectoris, myocardial infarction, arteriosclerosis, cerebrovascular disease, arrhythmia and the like.

Examples 44 and 45 were performed in order to verify the talin activity regulation induced by the compound of Formula 1 according to the present invention, and as a result, it was shown that the N-acylurea derivative inhibited the activity of talin by binding directly to the talin protein, and thus showed excellent antiplatelet effects. Accordingly, a pharmaceutical composition containing the compound of Formula 1 or the pharmaceutically acceptable salt thereof according to the present invention can be advantageously used to prevent or treat thrombotic cardiovascular disease by regulating the talin network.

It could be seen that the compound represented by the Formula 1 of the present invention inhibited angiogenesis through Example 46.

Figure 7:
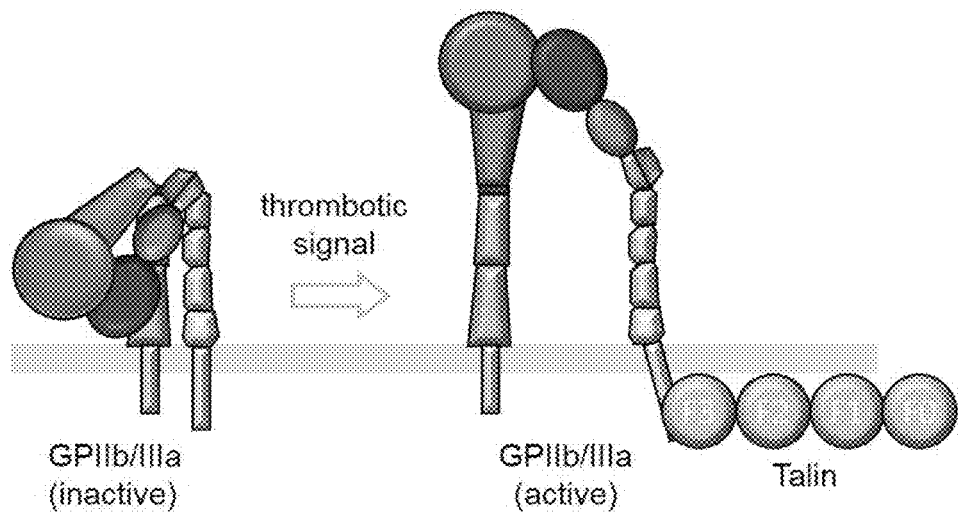
FIG. 7 schematically shows a mechanism by which the novel N-acylurea derivative of the present invention acts.
Figure 7:
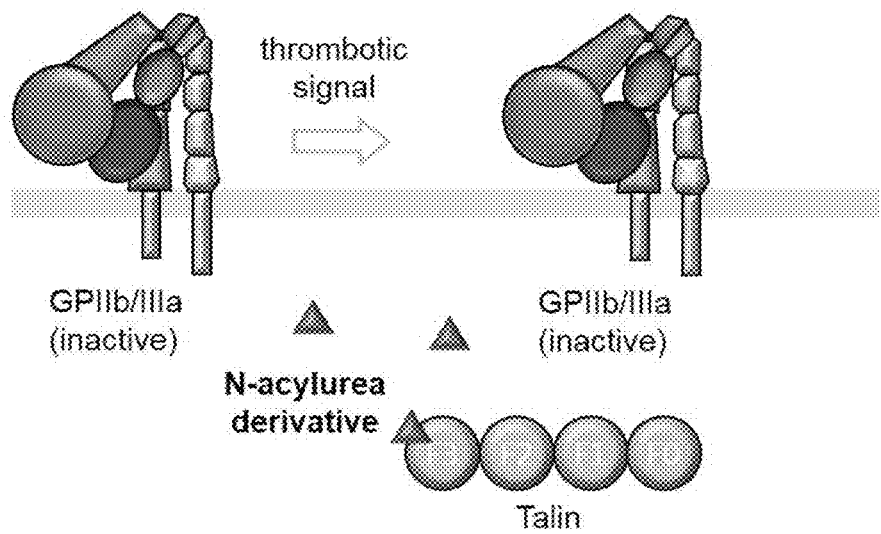

FIG. 7 shows the antiplatelet mechanism of the novel N-acylurea derivative of the present invention. As reported previously, a talin molecule binds to a GPIIb/IIIa protein, which is present in an inactive state, by a thrombotic signal, thereby causing a morphological change in the GPIIb/IIIa protein and activating the GPIIb/IIIa protein (FIG. 7A). However, the novel N-acylurea derivative of the present invention binds to the talin molecule, thereby inhibiting the talin molecule from binding directly to the GPIIb/IIIa protein. This maintains the GPIIb/IIIa protein in an inactive state (FIG. 7B).

Therefore, in still another aspect, the present invention is directed to a method of inhibiting the binding of a talin molecule to a GPIIb/IIIa protein by binding the compound of Formula 1 to the talin molecule.

The pharmaceutical composition of the present invention may further comprise a suitable carrier, excipient or diluent that is generally used in the preparation of drugs.

The pharmaceutical composition according to the present invention can be formulated according to a conventional method. For example, it may be formulated in the form of powders, granules, tablets, capsules, suspensions, emulsions, syrups, aerosols, agents for oral and external applications, suppositories, or sterile injection solutions. Carriers, excipients and diluents that can be contained in the composition according to the present invention include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

A pharmaceutical composition according to the present invention is formulated using diluents or excipients, such as fillers, extenders, binders, wetting agents, disintegrants or surfactants, which are commonly used. Solid Formulations for oral administration include tablets, pills, powders, granules, capsules, etc. Such solid Formulations are prepared by mixing the composition of present invention with at least one excipient, such as starch, calcium carbonate, sucrose, lactose, gelatin, etc. In addition to simple expedients, lubricants such as magnesium stearate, talc, etc. may also be added. Liquid Formulations for oral administration, such as suspensions, internal solutions, emulsions, syrups, etc., may include simple diluents, e.g., water and liquid paraffin, as well as various excipients, e.g., wetting agents, sweeteners, aromatics, preservatives, etc. Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

The composition of the present invention may be administered orally or parenterally. Any parenteral administration method can be used, and systemic or topical administration can be carried out, but the systemic administration is more preferable and the intravenous administration is most preferable.

The composition according to the present invention is administered in a pharmaceutically effective amount. As used herein, the term "pharmaceutically effective amount" refers to an amount sufficient to treat the disease at a reasonable benefit/risk ratio applicable for any medical treatment. The effective dosage level of the composition may be determined depending on the type of a patient's disease, the severity of disease, the activity of the drug, sensitivity to the drug, the time of administration, the route of administration and the excretion rate, the duration of treatment, factors including drugs used in combination with the composition, and other factors known in the medical field. The pharmaceutical composition of the present invention may be administered individually or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this amount can be easily determined by a person skilled in the art.

More specifically, the effective amount of the compound according to the present invention may vary depending on the patient's age, sex and body weight, and the compound of the present invention may generally be administered at a daily or two-day dose of from 0.1 to 100 mg, preferably from 0.5 to 10 mg per body weight 1 kg, or may be administered one time to three times per day. However, the dosage may be increased or decreased depending on the route of administration, the severity of the obesity, sex, body weight, age, and thus it is not intended to limit the scope of the present invention in any way.

In yet another aspect, the present invention is directed to a method of preparing the compound of Formula 1 above, comprising the steps of: (a) mixing and reacting 2-chloroacetamide, N,N-dimethylformamide, potassium carbonate and a nucleophilic reagent in a reactor, terminating the reaction by addition of water, followed by concentration to obtain acetamide; (b) adding oxalyl chloride to the obtained acetamide, replacing the inside of a reactor with argon, and then introducing dichloroethane into the reactor, and heating and stirring, followed by concentration to obtain acetyl isocyanate; and (c) adding methylene chloride to the obtained acetyl isocyanate, adding and reacting a nucleophilic reagent, and terminating the reaction by addition of water, followed by concentration to obtain an N-acylurea derivative.

In one embodiment of the present invention, the obtaining of acetamide in step (a) may comprise dilution with ethyl acetate, washing with water, drying an organic layer with $MgSO_4$, filtration, concentration under reduced pressure, and subjecting the concentrated compound to column chromatography with ethyl acetate/n-hexane.

In one embodiment of the present invention, the heating in step (a) may be performed at 60-100° C., preferably 75-90° C.

In one embodiment of the present invention, the obtaining of the N-acylurea derivative in step (c) may comprise diluting the residue, concentrated under reduced pressure, with a suitable solvent, washing with water, collecting an organic layer, drying the organic layer with MgSO$_4$, filtration, concentration under reduced pressure, and subjecting the concentrated compound to column chromatography.

In a further aspect, the present invention is directed to a method of preparing the compound of Formula 1 above, comprising the steps of: (a) mixing 2-chloroacetamide with oxalyl chloride in a reactor, replacing the inside of the reactor with argon, introducing dichloroethane into reactor, and heating and stirring, followed by concentration to obtain 2-chloroacetyl isocyanate; (b) adding methylene chloride to the obtained 2-chloroacetyl isocyanate, adding and reacting a nucleophilic reagent, and terminating the reaction by addition of water, followed by concentration to obtain carbamoyl 2-chloroacetamide; and (c) adding methanol to the obtained carbamoyl 2-chloroacetamide, adding and reacting a nucleophilic reagent while stirring, terminating the reaction by addition of water, extracting an N-acylurea derivative with an organic solvent, and then recovering the N-acylurea derivative.

In the present invention, the nucleophilic reagent may be selected from the group consisting of 4-bromo-3-methoxyanilin, 4-methoxybenzylamine, tryptamine, 2,4-dimethoxyaniline, 4-(benzyloxy)aniline, 2-fluoroaniline, Sesamol, 3-fluoropyridin-2-amine, 4-methoxyphenyl)methanamine, 4-(benzyloxy)aniline HCl, 2-Methoxyphenol, 4-phenoxyaniline, 3,5-bis(trifluoromethyl)phenol, 3-bromophenol, 4-bromo-3-methoxyaniline, 2,3-dimethylphenol), and 4-(benzyloxy)phenol.

In one embodiment of the present invention, the heating in step (a) may be performed at 60-100° C. preferably 75-90° C.

In one embodiment of the present invention, the obtaining of the 2-chloroacetyl isocyanate in step (b) may comprise diluting the residue, concentrated under reduced pressure, with a solvent, drying an organic layer with MgSO$_4$, filtration, concentration under reduced pressure, and then subjecting the concentrated compound to column chromatography.

In one embodiment of the present invention, the obtaining of the N-acylurea derivative in step (c) may comprise extracting the residue, concentrated under reduced pressure, with ethyl acetate, drying an organic layer with MgSO$_4$, filtration, concentration under reduced pressure, and then subjecting the concentrated compound to column chromatography.

EXAMPLES

Hereinafter, the present invention will be described in further detail with reference to examples. It will be obvious to a person having ordinary skill in the art that these examples are for illustrative purposes only and are not to be construed to limit the scope of the present invention.

Preparation Examples

Preparation Example 1

Preparation 1 of N-Acylurea Derivative

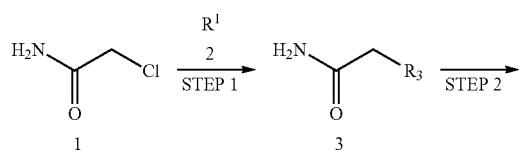

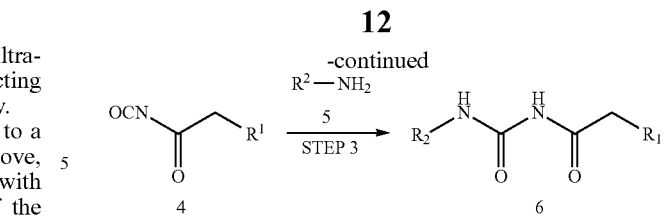

Step 1: Preparation of Acetamide Derivative (2)

Commercially available 2-chloroacetamide (1) was placed in a reactor, and N,N-dimethylformamide was added thereto. Potassium carbonate (3 equivalents) and a nucleophilic reagent (1 equivalent) were added, followed by stirring overnight at a suitable temperature. The reaction was terminated by adding H$_2$O to the reaction solution, followed by concentration under reduced pressure. The residue was diluted with ethyl acetate and washed with water, and the organic layer was dried with MgSO$_4$, filtered, and then concentrated under reduced pressure. The concentrated compound was subjected to column chromatography with ethyl acetate/n-hexane to obtain the desired compound (3).

Step 2: Preparation of Acetyl Isocyanate (4)

The acetamide (3) obtained in step 1 above and oxalyl chloride (1.5 equivalents) were placed in a reactor, and the inside of the reactor was replaced with argon, after which dichloroethane was introduced into the reactor. The reaction solution was heated to a temperature of 85° C. and stirred for 5 hours. After completion of the reaction, the desired compound (4) was obtained and used in the next reaction without a separate purification procedure.

Step 3: Preparation of N-Acylurea (6)

The acetyl isocyanate obtained in step 2 above was placed in a reactor, and methylene chloride was added thereto, followed by addition of a nucleophilic reagent (5) (1 equivalent). The reaction solution was stirred overnight at room temperature. The reaction was terminated by adding H$_2$O to the reaction solution, followed by concentration under reduced pressure. The residue was diluted with a suitable solvent and washed with water, and then the organic layer was collected. The organic layer was dried with MgSO$_4$, filtered, and then concentrated under reduced pressure. The concentrated compound was subjected to column chromatography to obtain the desired compound (6).

Preparation Example 2

Preparation 2 of N-Acylurea Derivatives

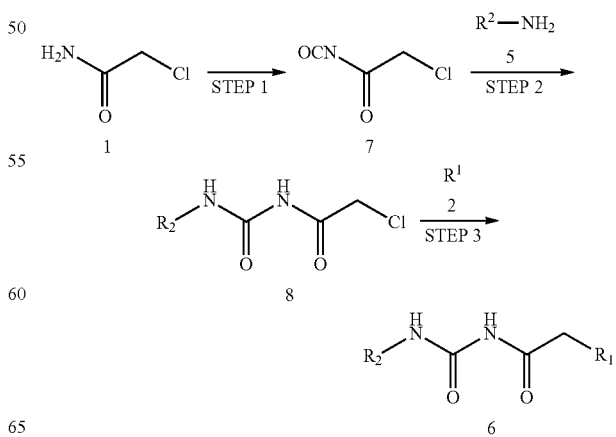

Step 1: Preparation of 2-Chloroacetyl Isocyanate (7)

Commercially available 2-chloroacetamide (1) and oxalyl chloride (1.5 equivalents) were placed in a reactor, and the inside of the reactor was replaced with argon, after which dichloroethane was introduced into the reactor. Next, the reaction solution was heated to a temperature of 85° C. and stirred for 5 hours. After completion of the reaction, the reaction solution was concentrated under reduced pressure, and the desired compound (7) was obtained and used in the next step without a separate purification procedure.

Step 2: Preparation of Carbamoyl 2-Chloroacetamide (8)

2-Chloroacetyl isocyanate (7) obtained in step 1 above was placed in a reactor, and methylene chloride was added thereto, followed by addition of a nucleophilic reagent (5) (1 equivalent). The reaction solution was stirred overnight at room temperature. The reaction solution was terminated by adding $H_2O$ to the reaction solution, followed by concentration under reduced pressure. The residue was diluted with a suitable solvent and washed with water, and then the organic layer was collected. The organic layer was dried with $MgSO_4$, filtered, and then concentrated under reduced pressure. The concentrated compound was subjected to column chromatography to obtain the desired compound (8).

Step 3: Preparation of N-Acylurea (6)

The compound carbamoyl 2-chloroacetamide (8)(1 equivalent) obtained in step 2 above was placed in a reactor, and methanol was added thereto, after which a nucleophilic reagent (3 equivalents) was added thereto at 0° C. The solution was stirred for 30 minutes at 0° C., and then stirred overnight at room temperature. The reaction was terminated by addition of $H_2O$, and the reaction solution was extracted with ethyl acetate. The organic layer was dried with $MgSO_4$, filtered, and then concentrated under reduced pressure. The concentrated compound was subjected to column chromatography to obtain the desired compound (6).

EXAMPLES

Example 1

Preparation of KCH-1510

N-((4-bromo-3-methoxyphenyl)carbamoyl)-2-(5-phenyl-2H-tetrazol-2-yl)acetamide (5a)

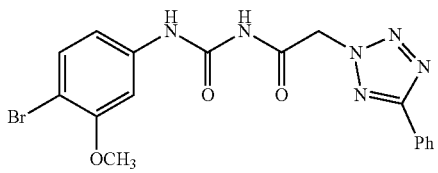 [SMILES: COc1cc(NC(=O)NC(=O)Cn2nnc(-c3ccccc3)n2)ccc1Br]

Step 1: Preparation of 2-(5-phenyl-2H-tetrazol-2-yl)acetamide (2a)

The process described in step 1 of Preparation Example 1 was performed using 5-phenyl-2H-tetrazole as a nucleophilic reagent.

Step 2: Preparation of 2-(5-phenyl-2H-tetrazol-2-yl)acetyl isocyanate (3a) 2-(5-phenyl-2H-tetrazol-2-yl)acetamide (2a)(69 mg, 0.340 mM) obtained in step 1 above, and oxalyl chloride (1.5 equivalents) (0.049 ml, 0.509 mM) were placed in a reactor, and the inside of the reactor was replaced with argon, after which dichloroethane (1.5 ml) was introduced into the reactor. Next, the reaction solution was heated to a temperature of 85° C., and then stirred for 5 hours. After completion of the reaction, the reaction was concentrated under reduced pressure and used in the next reaction without a separate purification procedure.

Step 3: Preparation of N-((4-bromo-3-methoxyphenyl)carbamoyl)-2-(5-phenyl-2H-tetrazol-2-yl)acetamide (5a) 2-(5-phenyl-2H-tetrazol-2-yl)acetyl isocyanate (3a) obtained in step 2 above was placed in a reactor, and methylene chloride (1.7 ml) was added thereto, followed by addition of 4-bromo-3-methoxyaniline (1 equivalent) (68.6 mg, 0.340 mM) as a nucleophilic reagent. The reaction solution was stirred overnight at room temperature. The reaction was terminated by adding $H_2O$ to the reaction solution, followed by concentration under reduced pressure. The residue was diluted with ethyl acetate and washed with water, and the organic layer was dried with $MgSO_4$, filtered, and then concentrated under reduced pressure. The concentrated compound was subjected to column chromatography with ethyl acetate: hexane (1:2) to obtain the desired compound (5a) (102 mg, 70%).

White solid, Rf 0.3 (Ethyl Acetate:n-Hexane=1:2); 1H-NMR (DMSO, 500 MHz) δ 8.08 (d, 2H, J=6.0 Hz), 7.61-7.56 (m, 2H), 7.48 (d, 1H, J=5.0 Hz), 7.30 (d, 1H, J=5.0 Hz), 7.16 (dd, 1H, J=2.5 Hz, 2.5 Hz), 5.90 (s, 1H), 3.80 (s, 2H), 3.35 (s, 3H); LC-MS [M+H]+432.

Example 2

Preparation of KCH-1511

N-((4-phenoxyphenyl)carbamoyl)-2-(5-phenyl-2H-tetrazol-2-yl)acetamide (5b)

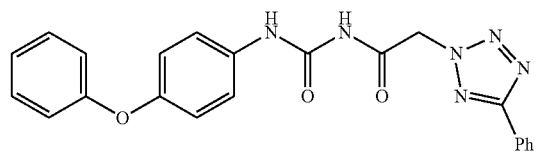 [SMILES: O=C(Cn1nnc(-c2ccccc2)n1)NC(=O)Nc1ccc(Oc2ccccc2)cc1]

Step 1: This step was performed in the same manner as step 1 of Example 1.

Step 2: This step was performed in the same manner as step 2 of Example 1.

Step 3: Preparation of N-((4-phenoxyphenyl)carbamoyl)-2-(5-phenyl-2H-tetrazol-2-yl)acetamide (5b)

This step was performed in the same manner as step 3 of Example 1, except that 4-phenoxyaniline (1 equivalent) (62.9 mg, 0.340 mM) was used instead of 4-bromo-3-methoxyaniline as the nucleophilic reagent, thereby obtaining the desired compound (5b) (91.5 mg, 65%).

White solid, Rf 0.25 (Ethyl Acetate:n-Hexane=1:2); 1H-NMR (DMSO, 500 MHz) δ 9.94 (s, 1H), 8.085 (dd, 1H, J=1.5 Hz, 9.9 Hz), 7.55 (m, 6.0H), 7.105 (t, 2H, J=7.5 Hz), 6.98 (t, 2H, J=9.0 Hz), 5.89 (s, 1H), 4.03 (q, 2H, J=6.5 Hz); LC-MS [M+H]+415.

Example 3

Preparation of KCH-1512

N-((4-methoxybenzyl)carbamoyl)-2-(5-phenyl-2H-tetrazol-2-yl)acetamide (5d)

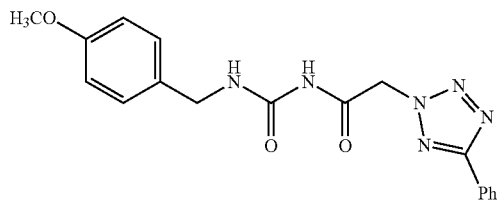 [SMILES: COc1ccc(CNC(=O)NC(=O)Cn2nnc(-c3ccccc3)n2)cc1]

Step 1: This step was performed in the same manner as step 1 of Example 1.

Step 2: This step was performed in the same manner as step 2 of Example 1.

Step 3: This step was performed in the same manner as step 3 of Example 1, except that 4-methoxybenzylamine (1 equivalent) (46.5 mg, 0.340 mM) was used instead of 4-bromo-3-methoxyaniline as the nucleophilic reagent, thereby obtaining the desired compound (5b) (87 mg, 70%).

White solid, Rf 0.35 (Ethyl Acetate:n-Hexane=1:1); 1H-NMR (DMSO, 500 MHz) δ 8.07 (dd, 2H, J=2.5 Hz, 8.5 Hz), 7.57 (d, 3H, J=6.5 Hz), 7.21 (d, 2H, J=8.5 Hz), 6.88 (d, 2H, J=8.5 Hz), 5.79 (s, 2H), 4.28 (d, 2H, J=6.15 Hz), 3.72 (s, 3H); LC-MS [M+H]+367.

<Example 4

Preparation of KCH-1513

N-((2-(3a,7a-dihydro-1H-indol-3-yl)ethyl)carbamoyl)-2-(5-phenyl-2H-tetrazol-2-yl)acetamide (5c)

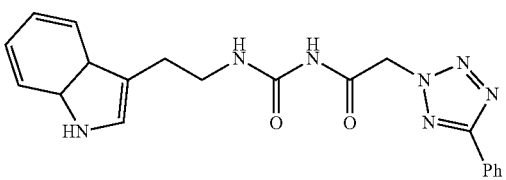 [SMILES: O=C(Cn1nnc(-c2ccccc2)n1)NC(=O)NCCC1=CNC2C=CC=CC12]

Step 1: This step was performed in the same manner as step 1 of Example 1.

Step 2: This step was performed in the same manner as step 2 of Example 1.

Step 3: This step was performed in the same manner as step 3 of Example 1, except that tryptamine (1 equivalent) (54.4 mg, 0.340 mM) was used instead of 4-bromo-3-methoxyaniline as the nucleophilic reagent, thereby obtaining the desired compound (5c) (103 mg, 78%).

Yellow solid, Rf 0.3 (Ethyl Acetate:n-Hexane=2:1); 1H-NMR (DMSO, 500 MHz) δ 10.79 (s, 1H), 8.07 (dd, 1H, J=2.0 Hz, 9.5 Hz), 7.56 (m, 3H), 7.31 (d, 1H, J=8.0 Hz), 7.14 (s, 1H), 7.04 (t, 2H, J=7.0 Hz), 6.95 (t, 2H, J=7.0 Hz), 5.77 (s, 1H), 4.03 (q, 2H, J=7.5 Hz), 3.45 (q, 2H, J=7.0 Hz), 2.87 (t, 2H, J=7.5 Hz); LC-MS [M+Na]+414.

Example 5

Preparation of KCH-1514

N-((2,4-dimethoxyphenyl)carbamoyl)-2-(5-phenyl-2H-tetrazol-2-yl)acetamide (5$_e$)

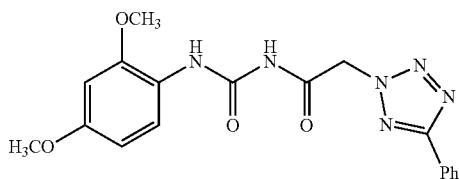 [SMILES: COc1ccc(NC(=O)NC(=O)Cn2nnc(-c3ccccc3)n2)c(OC)c1]

Step 1: This step was performed in the same manner as step 1 of Example 1.

Step 2: This step was performed in the same manner as step 2 of Example 1.

Step 3: This step was performed in the same manner as step 3 of Example 1, except that 2,4-dimethoxyaniline (1 equivalent) (52.0 mg, 0.340 mM) was used instead of 4-bromo-3-methoxyaniline as the nucleophilic reagent, thereby obtaining the desired compound (5e) (103 mg, 79%).

White solid, Rf 0.3 (Ethyl Acetate:n-Hexane=1:2); $^1$H-NMR (DMSO, 500 MHz) δ11.24 (s, 1H), 10.15 (s, 1H), 8.10 (dd, 1H, J=2.0 Hz, 9.5 Hz), 7.99 (d, 1H, J=9.0 Hz), 7.59 (d, 3H, J=7.5 Hz), 6.63 (d, 2H, J=2.75 Hz), 6.51 (dd, 1H, J=2.5 Hz, 11.5 Hz), 5.86 (s, 2H), 3.78 (s, 3H), 3.74 (s, 3H); LC-MS [M+Na]+405.

Example 6

Preparation of KCH-1515

N-((4-(benzyloxy)phenyl)carbamoyl)-2-(5-phenyl-2H-tetrazol-2-yl)acetamide (5)

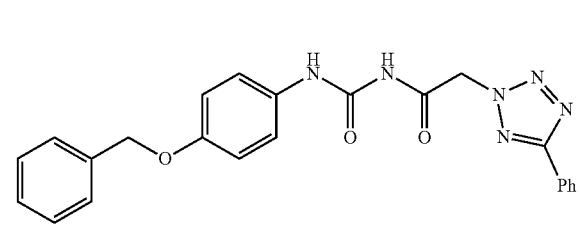 [SMILES: O=C(Cn1nnc(-c2ccccc2)n1)NC(=O)Nc1ccc(OCc2ccccc2)cc1]

Step 1: This step was performed in the same manner as step 1 of Example 1.

Step 2: This step was performed in the same manner as step 2 of Example 1.

Step 3: This step was performed in the same manner as step 3 of Example 1, except that 4-(benzyloxy)aniline (1 equivalent) (116.0 mg, 0.492 mM) was used instead of 4-bromo-3-methoxyaniline as the nucleophilic reagent, thereby obtaining the desired compound (5f) (147 mg, 70%).

White solid, Rf 0.3 (Ethyl Acetate:n-Hexane=1:2); 1H-NMR (DMSO, 500 MHz) δ 11.24 (s, 1H), 9.80 (s, 1H), 8.08 (s, 2H), 7.58 (s, 3H), 7.42-7.32 (m, 4H), 6.97 (s, 2H), 5.89 (s, 2H), 5.07 (s, 2H); LC-MS [M+H]+430.

Example 7

Preparation of KCH-1516

N-((2-fluorophenyl)carbamoyl)-2-(5-phenyl-2H-tetrazol-2-yl)acetamide (5g)

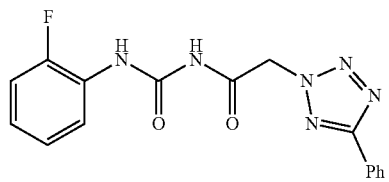 [SMILES: O=C(Cn1nnc(-c2ccccc2)n1)NC(=O)Nc1ccccc1F]

Step 1: This step was performed in the same manner as step 1 of Example 1.

Step 2: This step was performed in the same manner as step 2 of Example 1.

Step 3: This step was performed in the same manner as step 3 of Example 1, except that 2-fluoroaniline (1 equivalent) (0.049 mg, 0.51 mM) was used instead of 4-bromo-3-methoxyaniline as the nucleophilic reagent, thereby obtaining the desired compound (5g) (121 mg, 70%).

White solid, Rf 0.3 (Ethyl Acetate:n-Hexane=1:2); 1H-NMR (DMSO, 500 MHz) δ 10.18 (s, 1H), 8.11-8.08 (m, 3H), 7.60-7.56 (m, 3H), 7.30-7.13 (m, 3H), 5.90 (s, 2H); LC-MS [M+H]+341.

Example 8

Preparation of KCH-1517

2-(benzo[d][1,3]dioxol-5-yloxy)-N-((3-fluoropyridin-2-yl)carbamoyl) acetamide (5i)

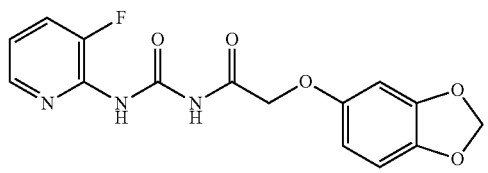 [SMILES: O=C(COc1ccc2c(c1)OCO2)NC(=O)Nc1ncccc1F]

Step 1: The process described in step 1 of Preparation Example 1 was performed using sesamol as a nucleophilic reagent.

Step 2: This step was performed in the same manner as step 2 of Example 1, except that 2-(benzo[d][1,3]dioxol-5-yloxy)acetamide (2i) (60 mg, 0.335 mM) was used instead of 2-(5-phenyl-2H-tetrazol-2-yl)acetamide (2a).

Step 3: This step was performed in the same manner as step 3 of Example 1, except that 2-(benzo[d][1,3]dioxol-5-yloxy)acetyl isocyanate (3i) obtained in step 2 was used instead of 2-(5-phenyl-2H-tetrazol-2-yl)acetyl isocyanate (3a), and 3-fluoropyridin-2-amine (1 equivalent) (38.7 mg, 0.345 mM) was used instead of 4-bromo-3-methoxyaniline as the nucleophilic reagent, thereby obtaining the desired compound (5i) (90.8 mg, 79%).

Yellow solid, Rf 0.3 (Ethyl Acetate:n-Hexane=1:2); 1H-NMR (DMSO, 500 MHz) δ 10.34 (s, 1H), 8.43 (s, 1H), 7.215 (d. 1H, J=8.5 Hz), 6.890-6.790 (m, 3H), 6.6395 (s, 1H), 6.33 (d, 1H, J=8.75), 4.64 (s, 2H), 4.30 (dd, 1H, J=5.5 Hz); LC-MS [M+Na]+357.

Example 9

Preparation of KCH-1518

2-(benzo[d][1,3]dioxol-5-yloxy)-N-((4-bromo-3-methoxyphenyl)carbamoyl) acetamide (5j)

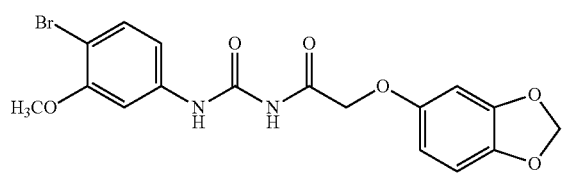 [SMILES: COc1cc(NC(=O)NC(=O)COc2ccc3c(c2)OCO3)ccc1Br]

Step 1: This step was performed in the same manner as step 1 of Example 8.

Step 2: This step was performed in the same manner as step 2 of Example 8.

Step 3: This step was performed in the same manner as step 3 of Example 8, except that 4-bromo-3-methoxyaniline (69.8 mg, 0.345 mM) was used instead of 3-fluoropyridin-2-amine as the nucleophilic reagent, thereby obtaining the desired compound (5j) (96 mg, 66%).

Yellow solid, Rf 0.3 (Ethyl Acetate:n-Hexane=1:2); 1H-NMR (DMSO, 500 MHz) δ 10.69 (s, 1H), 10.26 (s, 1H), 7.49 (d, 1H, J=8.5 Hz), 7.31 (s, 1H), 7.14 (d, 1H, J=9.0 Hz), 6.82 (d, 1H, J=8.25 Hz), 6.68 (s, 1H), 6.38 (d, 1H, J=8.75 Hz), 5.97 (s, 2H), 4.75 (s, 2H), 3.83 (s, 3H); LC-MS [M+Na]+446.

Example 10

Preparation of KCH-1519

2-(benzo[d][1,3]dioxol-5-yloxy)-N-((4-phenoxyphenyl)carbamoyl)acetamide (5k)

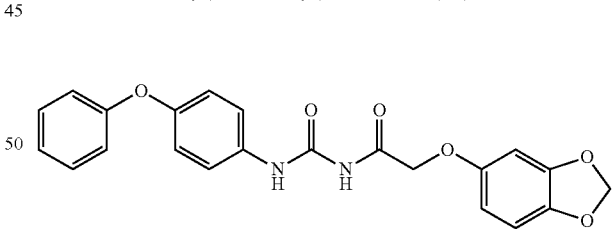

Step 1: This step was performed in the same manner as step 1 of Example 8.

Step 2: This step was performed in the same manner as step 2 of Example 8.

Step 3: This step was performed in the same manner as step 3 of Example 8, except that 4-phenoxyaniline (64 mg, 0.345 mM) was used instead of 3-fluoropyridin-2-amine as the nucleophilic reagent, thereby obtaining the desired compound (5k) (98 mg, 70%).

Gray solid, Rf0.4 (Ethyl Acetate:n-Hexane=1:3); 1H-NMR (DMSO, 500 MHz) δ 10.63 (s, 1H), 10.18 (s, 1H), 7.53 (d, 2H, J=8.5 Hz), 7.37 (t, 2H, J=8.5 Hz), 7.158 (t, 4H, J=7.0 Hz), 6.82 (d, 1H, J=8.5 Hz), 6.68 (s, 1H), 6.38 (dd, 1H, J=2.5 Hz, 11 Hz), 5.97 (s, 2H), 4.73 (s, 2H); LC-MS [M+H]+408.

Example 11

Preparation of KCH-1520

2-(benzo[d][1,3]dioxol-5-yloxy)-N-((4-methoxybenzyl)carbamoyl)acetamide (5l)

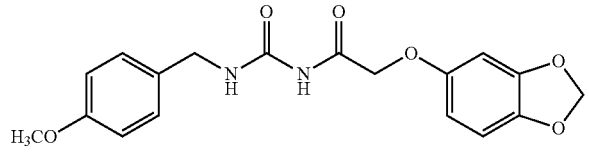 [SMILES: COc1ccc(CNC(=O)NC(=O)COc2ccc3c(c2)OCO3)cc1]

Step 1: This step was performed in the same manner as step 1 of Example 8.
Step 2: This step was performed in the same manner as step 2 of Example 8.
Step 3: This step was performed in the same manner as step 3 of Example 8, except that (4-methoxyphenyl) methanamine (47.4 mg, 0.345 mM) was used instead of 3-fluoropyridin-2-amine as the nucleophilic reagent, thereby obtaining the desired compound (5l) (86.5 mg, 70%).
Yellow solid, Rf 0.3 (Ethyl Acetate:n-Hexane=1:2); 1H-NMR (DMSO, 500 MHz) δ 11.13 (s, 1H), 10.23 (s, 1H), 8.227 (d, 1H, J=4.5 Hz), 7.8 (t, 1H, J=9.8 Hz), 7.345-7.31 (m, 2H), 6.82 (d, 1H, J=8.0 Hz), 6.69 (s, 1H), 5.97 (s, 2H), 4.77 (s, 2H), 1.24 (s, 2H); LC-MS [M+Na]+382.

Example 12

Preparation of KCH-1521

N42-(1H-indol-3-yl)ethyl)carbamoyl)-2-(benzo[d][1,3]dioxol-5-yloxy) acetamide (5m)

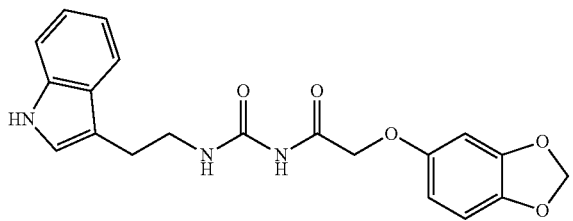 [SMILES: O=C(COc1ccc2c(c1)OCO2)NC(=O)NCCc1c[nH]c2ccccc12]

Step 1: This step was performed in the same manner as step 1 of Example 8.
Step 2: This step was performed in the same manner as step 2 of Example 8.
Step 3: This step was performed in the same manner as step 3 of Example 8, except that tryptamine (55.3 mg, 0.345 mM) was used instead of 3-fluoropyridin-2-amine as the nucleophilic reagent, thereby obtaining the desired compound (5m) (92 mg, 70%).
Yellow solid, Rf 0.3 (Ethyl Acetate:n-Hexane=1:2); 1H-NMR (DMSO, 500 MHz) δ 10.81 (s, 1H), 10.26 (s, 1H), 7.56 (d, 1H, J=7.5 Hz), 7.33 (d, 1H, J=8.0 Hz), 7.15 (s, 1H), 7.06 (t, 1H, J=7.5 Hz), 6.96 (t, 1H, J=7.0 Hz), 6.80 (d, 1H, J=8.5 Hz), 6.64 (d, 1H, J=2.5 Hz), 6.33 (dd, 1H, J=2.5 Hz, 11.0 Hz), 5.96 (s, 2H), 4.61 (s, 2H), 3.46 (q, 2H, J=7.4 Hz), 2.88 (t, 2H, J=7.0 Hz).

Example 13

Preparation of KCH-1522

2-(benzo[d][1,3]dioxol-5-yloxy)-N-((2,4-dimethoxyphenyl)carbamoyl) acetamide (5n)

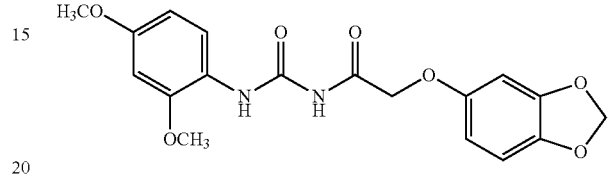

Step 1: This step was performed in the same manner as step 1 of Example 8.
Step 2: This step was performed in the same manner as step 2 of Example 8.
Step 3: This step was performed in the same manner as step 3 of Example 8, except that 2,4-dimethoxyaniline (52.9 mg, 0.345 mM) was used instead of 3-fluoropyridin-2-amine as the nucleophilic reagent, thereby obtaining the desired compound (5n) (90 mg, 70%).
Brown solid, Rf 0.3 (Ethyl Acetate:n-Hexane=1:2); 1H-NMR (DMSO, 500 MHz) δ 10.66 (s, 1H), 10.39 (s, 1H), 7.99 (d, 1H, J=8.8 Hz), 6.83-6.80 (m, 1H), 6.65 (dd, 2H, J=2.5 Hz, 17.2 Hz), 6.50 (dd, 1H, J=2.5 Hz, 11.3 Hz), 6.36 (dd, 1H, J=2.5 Hz, 11.0 Hz), 5.97 (d, 2H, J=5.3 Hz), 4.70 (s, 2H), 3.83 (s, 3H), 3.74 (s, 3H); LC-MS [M+H]+375.

Example 14

Preparation of KCH-1523

2-(benzo[d][1,3]dioxol-5-yloxy)-N-((4-(benzyloxy)phenyl)carbamoyl) acetamide (5o)

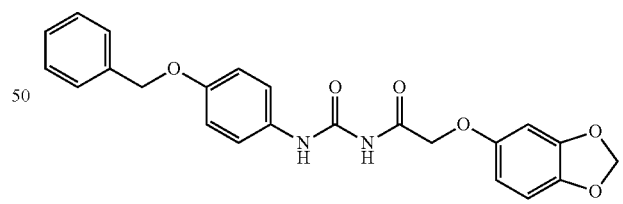

Step 1: This step was performed in the same manner as step 1 of Example 8.
Step 2: This step was performed in the same manner as step 2 of Example 8.
Step 3: This step was performed in the same manner as step 3 of Example 8, except that 4-(benzyloxy)aniline HCl (81.4 mg, 0.345 mM) was used instead of 3-fluoropyridin-2-amine as the nucleophilic reagent, thereby obtaining the desired compound (5o) (60.9 mg, 42%).
Brown solid, Rf 0.35 (Ethyl Acetate:n-Hexane=1:2); 1H-NMR (DMSO, 500 MHz) δ 10.59 (s, 1H), 10.04 (s, 1H), 7.45-7.31 (m, 6H), 6.98 (d, 2H, J=9.3 Hz), 6.82 (d, 1H, J=8.3

Hz), 6.68 (d, 1H, J=2.5 Hz), 6.37 (dd, 1H, J=2.5 Hz, 11.0 Hz), 5.97 (s, 2H), 5.08 (s, 2H), 4.72 (s, 2H); LC-MS [M+H]+421.

Example 15

Preparation of KCH-1524

2-(benzo[d][1,3]dioxo1-5-yloxy)-N-((2-fluorophenyl)carbamoyl)acetamide (5p)

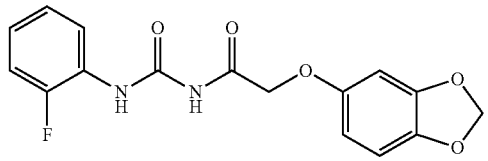 [SMILES: O=C(COc1ccc2c(c1)OCO2)NC(=O)Nc1ccccc1F]

Step 1: This step was performed in the same manner as step 1 of Example 8.
Step 2: This step was performed in the same manner as step 2 of Example 8.
Step 3: This step was performed in the same manner as step 3 of Example 8, except that 2-fluoroaniline (0.033 ml, 0.345 mM) was used instead of 3-fluoropyridin-2-amine as the nucleophilic reagent, thereby obtaining the desired compound (5p) (43.5 mg, 38%).

White solid, Rf 0.35 (Ethyl Acetate:n-Hexane=1:3); 1H-NMR (DMSO, 500 MHz) δ 10.89 (s, 1H), 10.48 (s, 1H), 8.13 (t, 1H, J=7.6 Hz), 7.29 (t, 1H, J=10.1 Hz), 7.21-7.11 (m, 2H), 6.82 (d, 1H, J=8.5 Hz), 6.69 (d, 1H, J=6.3 Hz), 6.38 (dd, 1H, J=2.5 Hz, 11.0 Hz), 5.97 (s, 2H), 4.74 (s, 2H); LC-MS [M+H]+333.

Example 16

Preparation of KCH-1525

N-((3-fluoropyridin-2-yl)carbamoyl)-2-(2-methoxyphenoxy)acetamide (5q)

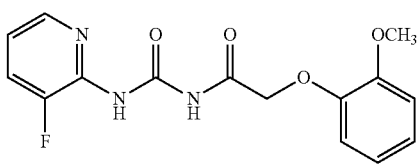 [SMILES: COc1ccccc1OCC(=O)NC(=O)Nc1ncccc1F]

Step 1: The process described in step 1 of Preparation Example 1 was performed using 2-Methoxyphenol as a nucleophilic reagent.
Step 2: This step was performed in the same manner as step 2 of Example 1, except that 2-(2-methoxyphenoxy)acetamide (2q) (40 mg, 0.2207 mM) was used instead of 2-(5-phenyl-2H-tetrazol-2-yl)acetamide (2a).
Step 3: This step was performed in the same manner as step 3 of Example 1, except that 2-(2-methoxyphenoxy)acetyl isocyanate (3q) obtained in step 2 was used instead of 2-(5-phenyl-2H-tetrazol-2-yl)acetyl isocyanate (3a), and 3-fluoropyridin-2-amine (1 equivalent) (24.7 mg, 0.221 mM) was used instead of 4-bromo-3-methoxyaniline as the nucleophilic reagent, thereby obtaining the desired compound (5q) (17 mg, 24%).

White solid, Rf 0.4 (Ethyl Acetate:n-Hexane=1:1); 1H-NMR (DMSO, 500 MHz) δ 11.08 (s, 1H), 10.22 (s, 1H), 8.21 (s, 1H), 7.79 (t, 1H, J=9.5 Hz), 7.33 (m, 2H), 6.95 (m, 2H), 4.83 (s, 2H), 3.79 (s, 3H); LC-MS [M+Na]+343.

Example 17

Preparation of KCH-1526

N-((4-bromo-3-methoxyphenyl)carbamoyl)-2-(2-methoxyphenoxy)acetamide (5r)

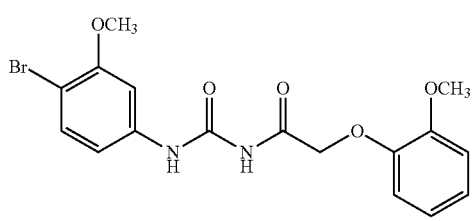 [SMILES: COc1cc(NC(=O)NC(=O)COc2ccccc2OC)ccc1Br]

Step 1: This step was performed in the same manner as step 1 of Example 16.
Step 2: This step was performed in the same manner as step 2 of Example 16.
Step 3: This step was performed in the same manner as step 3 of Example 16, except that 4-bromo-3-methoxyaniline (44.6 mg, 0.221 mM) was used instead of 3-fluoropyridin-2-amine as the nucleophilic reagent, thereby obtaining the desired compound (5r) (63 mg, 70%).

White solid, Rf 0.3 (Ethyl Acetate:n-Hexane=1:3); 1H-NMR (DMSO, 500 MHz) δ 10.72 (s, 1H), 10.31 (s, 1H), 7.49 (d, 1H, J=7.5 Hz), 7.31 (s, 1H), 7.16 (d, 1H, J=9.0 Hz), 7.01 (d, 1H, J=7.5 Hz), 6.96-6.85 (m, 3H), 4.81 (s, 2H), 3.82 (s, 3H), 3.78 (s, 3H); LC-MS [M+Na]+431.

Example 18

Preparation of KCH-1527

2-(2-methoxyphenoxy)-N-((4-phenoxyphenyl)carbamoyl)acetamide (5s)

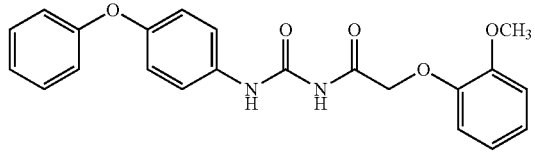 [SMILES: COc1ccccc1OCC(=O)NC(=O)Nc1ccc(Oc2ccccc2)cc1]

Step 1: This step was performed in the same manner as step 1 of Example 16.
Step 2: This step was performed in the same manner as step 2 of Example 16.
Step 3: This step was performed in the same manner as step 3 of Example 15, except that 4-phenoxyaniline (51.1 mg, 0.276 mM) was used instead of 3-fluoropyridin-2-amine as the nucleophilic reagent, thereby obtaining the desired compound (5s) (62 mg, 57%).

Yellow solid, Rf 0.32 (Ethyl Acetate:n-Hexane=1:3); 1H-NMR (DMSO, 500 MHz) δ 10.58 (s, 1H), 10.16 (s, 1H), 7.54 (d, 2H, J=10.0 Hz), 7.37 (t, 2H, J=8.0 Hz), 7.12 (t, 2H, J=7.5 Hz), 7.02-6.86 (m, 7H), 4.80 (s, 2H), 3.80 (s, 3H); LC-MS [M+H]+393.

Example 19

Preparation of KCH-1528

N-((4-methoxybenzyl)carbamoyl)-2-(2-methoxyphenoxy)acetamide (5t)

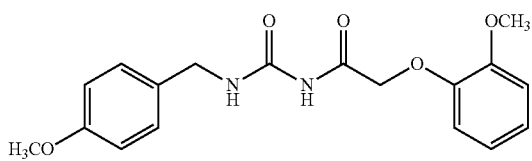 [SMILES: COc1ccc(CNC(=O)NC(=O)COc2ccccc2OC)cc1]

Step 1: This step was performed in the same manner as step 1 of Example 16.
Step 2: This step was performed in the same manner as step 2 of Example 16.
Step 3: This step was performed in the same manner as step 3 of Example 16, except that 4-methoxyphenyl)methanamine (0.029 ml, 0.221 mM) was used instead of 3-fluoropyridin-2-amine as the nucleophilic reagent, thereby obtaining the desired compound (5t) (31 mg, 41%).
White solid, Rf 0.3 (Ethyl Acetate:n-Hexane=1:2); 1H-NMR (DMSO, 500 MHz) δ 10.25 (s, 1H), 8.44 (s, 1H), 7.22 (d, 3H=7.5 Hz), 7.01-6.84 (m, 5H), 4.70 (s, 2H), 4.30 (s, 3H), 3.77 (s, 3H), 3.73 (s, 3H); LC-MS [M+H]+345.

Example 20

Preparation of KCH-1529

N-((2-(1H-indol-3-yl)ethyl)carbamoyl)-2-(2-methoxyphenoxy)acetamide (5u)

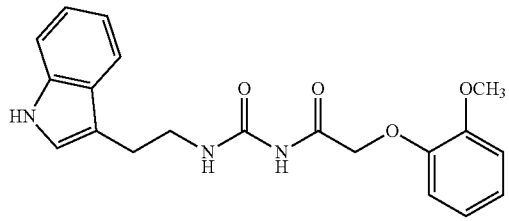 [SMILES: COc1ccccc1OCC(=O)NC(=O)NCCc1c[nH]c2ccccc12]

Step 1: This step was performed in the same manner as step 1 of Example 16.
Step 2: This step was performed in the same manner as step 2 of Example 16.
Step 3: This step was performed in the same manner as step 3 of Example 16, except that tryptamine (53 mg, 0.331 mM) was used instead of 3-fluoropyridin-2-amine as the nucleophilic reagent, thereby obtaining the desired compound (5u) (94.6 mg, 76%).
White solid, Rf 0.3 (Ethyl Acetate:n-Hexane=1:2); 1H-NMR (DMSO, 500 MHz) δ 10.82 (s, 1H), 10.20 (s, 1H), 7.56 (d, 1H, J=7.8 Hz), 7.33 (s, 1H), 7.16 (s, 1H), 7.08-6.86 (m, 5H), 4.68 (s, 2H), 3.78 (s, 2H), 3.46 (q, 2H, J=7.5 Hz), 3.32 (s, 3H), 2.88 (t, 2H, J=7.0 Hz); LC-MS [M+H]+369.

Example 21

Preparation of KCH-1530

N-((2,4-dimethoxyphenyl)carbamoyl)-2-(2-methoxyphenoxy)acetamide (5v)

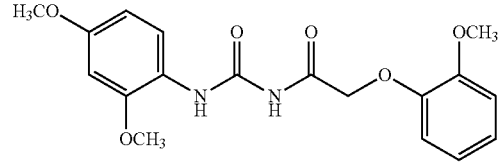 [SMILES: COc1ccc(NC(=O)NC(=O)COc2ccccc2OC)c(OC)c1]

Step 1: This step was performed in the same manner as step 1 of Example 16.
Step 2: This step was performed in the same manner as step 2 of Example 16.
Step 3: This step was performed in the same manner as step 3 of Example 16, except that 2,4-dimethoxyaniline (51 mg, 0.331 mM) was used instead of 3-fluoropyridin-2-amine as the nucleophilic reagent, thereby obtaining the desired compound (5v) (83.4 mg, 70%).
Brown solid, Rf 0.3 (Ethyl Acetate:n-Hexane=1:5); 1H-NMR (DMSO, 500 MHz) δ 10.61 (s, 1H), 10.39 (s, 1H), 7.99 (d, 1H, J=8.8 Hz), 7.02 (d, 1H, J=8.0 Hz), 6.97-6.86 (m, 4H), 6.65 (d, 1H, J=2.5 Hz), 6.51 (dd, 1H, J=2.5 Hz, 11.4 Hz), 4.77 (s, 2H), 3.83 (s, 2H), 3.80 (s, 3H), 3.74 (s, 3H); LC-MS [M+H]+361.

Example 22

Preparation of KCH-1531

N-((4-(benzyloxy)phenyl)carbamoyl)-2-(2-methoxyphenoxy)acetamide (5w)

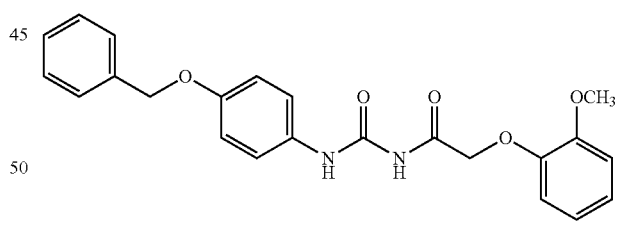

Step 1: This step was performed in the same manner as step 1 of Example 16.
Step 2: This step was performed in the same manner as step 2 of Example 16.
Step 3: This step was performed in the same manner as step 3 of Example 16, except that 4-(benzyloxy)aniline (52 mg, 0.221 mM) was used instead of 3-fluoropyridin-2-amine as the nucleophilic reagent, thereby obtaining the desired compound (5w) (56.5 mg, 63%).
Brown solid, Rf 0.3 (Ethyl Acetate:n-Hexane=1:3); 1H-NMR (DMSO, 500 MHz) δ 10.58 (s, 1H), 10.06 (s, 1H), 7.53-6.88 (m, 13H), 5.07 (s, 2H), 4.78 (s, 2H), 3.79 (s, 3H); LC-MS [M+Na]+430.

Example 23

Preparation of KCH-1532

N-((2-fluorophenyl)carbamoyl)-2-(2-methoxyphenoxy)acetamide (5x)

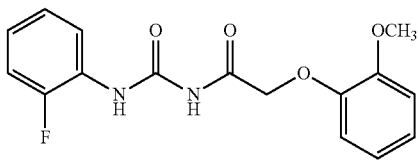 [SMILES: COc1ccccc1OCC(=O)NC(=O)Nc1ccccc1F]

Step 1: This step was performed in the same manner as step 1 of Example 16.
Step 2: This step was performed in the same manner as step 2 of Example 16.
Step 3: This step was performed in the same manner as step 3 of Example 16, except that 2-fluoroaniline (0.033 ml, 0.331 mM) was used instead of 3-fluoropyridin-2-amine as the nucleophilic reagent, thereby obtaining the desired compound (5x) (74 mg, 70%).

White solid, Rf 0.4 (Ethyl Acetate:n-Hexane=1:4); 1H-NMR (DMSO, 500 MHz) δ 10.86 (s, 1H), 10.48 (s, 1H), 8.13 (t, 1H, J=8.0 Hz), 7.3 (t, 1H, J=8.0 Hz), 7.21-7.11 (m, 2H), 7.03-6.86 (m, 4H), 4.81 (s, 2H), 3.80 (s, 3H); LC-MS [M+H]+319.

Example 24

Preparation of KCH-1533

2-(3,5-bis(trifluoromethyl)phenoxy)-N-((3-fluoropyridin-2-yl)carbamoyl) acetamide (5y)

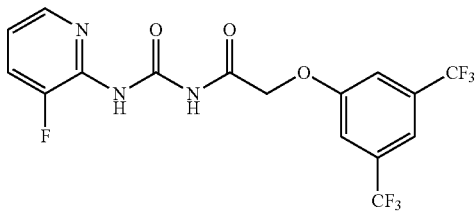

Step 1: The process described in step 1 of Preparation Example 1 was performed using 3,5-bis(trifluoromethyl) phenol as a nucleophilic reagent.
Step 2: This step was performed in the same manner as step 2 of Example 1, except that 2-(3,5-bis(trifluoromethyl) phenoxy)acetamide (2y) (70 mg, 0.244 mM) obtained in step 1 was used instead of 2-(5-phenyl-2H-tetrazol-2-yl) acetamide (2a).
Step 3: This step was performed in the same manner as step 3 of Example 1, except that 2-(3,5-bis(trifluoromethyl) phenoxy)acetyl isocyanate (3y) obtained in step 2 was used instead of 2-(5-phenyl-2H-tetrazol-2-yl)acetyl isocyanate (3a), and 3-fluoropyridin-2-amine (1 equivalent) (27 mg, 0.243 mM) was used instead of 4-bromo-3-methoxyaniline as the nucleophilic reagent, thereby obtaining the desired compound (5y) (72 mg, 70%).

White solid, Rf 0.4 (Ethyl Acetate:n-Hexane=1:4); 1H-NMR (DMSO, 500 MHz) δ 11.23 (s, 1H), 10.17 (s, 1H), 8.24 (s, 1H), 7.81-7.68 (m, 4H), 7.34 (s, 1H), 5.16 (s, 2H); LC-MS [M+H]+427.

Example 25

Preparation of KCH-1534

2-(3,5-bis(trifluoromethyl)phenoxy)-N-((4-bromo-3-methoxyphenyl) carbamoyl)acetamide (5z)

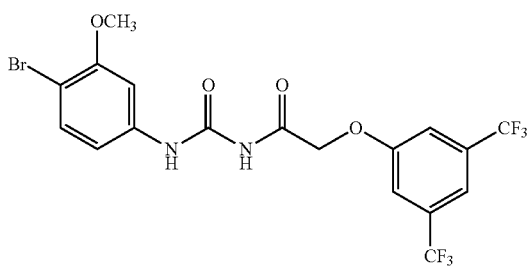 [SMILES: COc1cc(NC(=O)NC(=O)COc2cc(C(F)(F)F)cc(C(F)(F)F)c2)ccc1Br]

Step 1: This step was performed in the same manner as step 1 of Example 24.
Step 2: This step was performed in the same manner as step 2 of Example 24.
Step 3: This step was performed in the same manner as step 3 of Example 24, except that 4-bromo-3-methoxyaniline (52.5 mg, 0.259 mM) was used instead of 3-fluoropyridin-2-amine as the nucleophilic reagent, thereby obtaining the desired compound (5z) (29 mg, 22%).

Yellow solid, Rf 0.3 (Ethyl Acetate:n-Hexane=1:4); 1H-NMR (DMSO, 500 MHz) δ 10.75 (s, 1H), 10.15 (s, 1H), 7.72 (s, 1H), 7.68 (s, 1H), 7.5 (d, 2H, J=8.8 Hz), 7.3 (d, 1H, J=2.5 Hz), 7.2 (dd, 1H, J=2.3 Hz, 11.0 Hz), 3.82 (s, 2H), 3.2 (d, 3H, J=5.0 Hz).

Example 26

Preparation of KCH-1535

2-(3,5-bis(trifluoromethyl)phenoxy)-N-((4-bromo-3-methoxyphenyl) carbamoyl)acetamide (5aa)

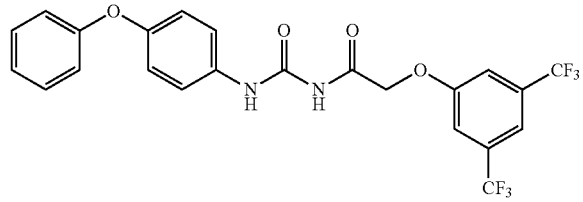 [SMILES: O=C(COc1cc(C(F)(F)F)cc(C(F)(F)F)c1)NC(=O)Nc1ccc(Oc2ccccc2)cc1]

Step 1: This step was performed in the same manner as step 1 of Example 24.
Step 2: This step was performed in the same manner as step 2 of Example 24.
Step 3: This step was performed in the same manner as step 3 of Example 24, except that 4-phenoxyaniline (45.0 mg, 0.243 mM) was used instead of 3-fluoropyridin-2-amine as the nucleophilic reagent, thereby obtaining the desired compound (5aa) (98 mg, 81%).

White solid, Rf 0.3 (Ethyl Acetate:n-Hexane=1:5); 1H-NMR (DMSO, 500 MHz) δ 10.71 (s, 1H), 10.06 (s, 1H), 7.7 (d, 3H, J=22.5 Hz), 7.54 (s, 2H), 7.37 (s, 2H), 7.11 (s, 1H), 7.0 (s, 4H), 5.11 (s, 2H); LC-MS [M+Na]+521.

Example 27

Preparation of KCH-1536

2-(3,5-bis(trifluoromethyl)phenoxy)-N-((4-methoxybenzyl)carbamoyl) acetamide (5ab)

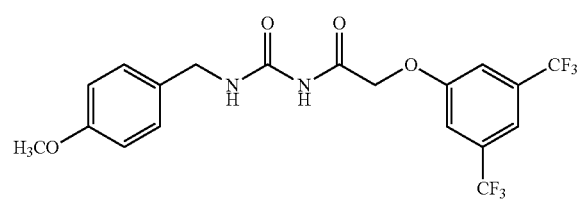 [SMILES: COc1ccc(CNC(=O)NC(=O)COc2cc(C(F)(F)F)cc(C(F)(F)F)c2)cc1]

Step 1: This step was performed in the same manner as step 1 of Example 24.
Step 2: This step was performed in the same manner as step 2 of Example 24.
Step 3: This step was performed in the same manner as step 3 of Example 24, except that 4-methoxyphenyl)methanamine (0.031 8 ml, 0.243 mM) was used instead of 3-fluoropyridin-2-amine as the nucleophilic reagent, thereby obtaining the desired compound (5ab) (66.7 mg, 61%)

White solid, Rf 0.3 (Ethyl Acetate:n-Hexane=1:3); 1H-NMR (DMSO, 500 MHz) δ 10.47 (s, 1H), 8.40 (s, 1H), 7.68-7.64 (m, 3H), 7.22-7.16 (m, 2H), 6.88-6.84 (m, 2H), 5.00 (s, 2H), 4.29 (d, 2H, J=5.8 Hz), 3.72 (s, 3H); LC-MS [M+Na]+473.

Example 28

Preparation of KCH-1537

N-((2-(1H-indol-3-yl)ethyl)carbamoyl)-2-(3,5-bis(trifluoromethyl)phenoxyl acetamide (5ac)

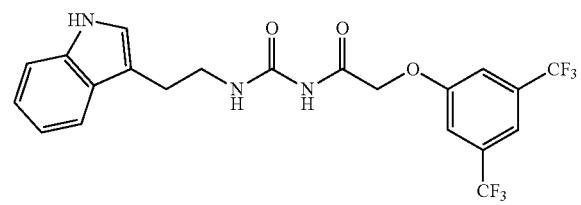 [SMILES: O=C(COc1cc(C(F)(F)F)cc(C(F)(F)F)c1)NC(=O)NCCc1c[nH]c2ccccc12]

Step 1: This step was performed in the same manner as step 1 of Example 24.
Step 2: This step was performed in the same manner as step 2 of Example 24.
Step 3: This step was performed in the same manner as step 3 of Example 24, except that tryptamine (33.5 mg, 0.209 mM) was used instead of 3-fluoropyridin-2-amine as the nucleophilic reagent, thereby obtaining the desired compound (5ac) (69 mg, 70%).

White solid, Rf 0.2 (Ethyl Acetate:n-Hexane=1:2); 1H-NMR (DMSO, 500 MHz) δ 10.81 (s, 1H), 10.40 (s, 1H), 8.14 (s, 1H), 7.68 (d, 2H, J=5.5 Hz), 7.56 (d, 1H, J=8.0 Hz), 7.33 (d, 1H, J=8.3 Hz), 7.15 (d, 1H, J=2.5 Hz), 7.05 (t, 1H, J=7.5 Hz), 6.96 (t, 1H, J=7.5 Hz), 4.98 (s, 2H), 3.46 (q, 2H, J=7.4 Hz), 2.88 (t, 2H, J=7.3 Hz); LC-MS [M+H]+475.

Example 29

Preparation of KCH-1538

2-(3,5-bis(trifluoromethyl)phenoxy)-N-((2,4-dimethoxyphenyl) carbamoyl)acetamide (5ad)

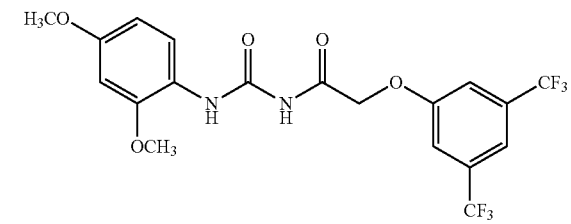 [SMILES: COc1ccc(NC(=O)NC(=O)COc2cc(C(F)(F)F)cc(C(F)(F)F)c2)c(OC)c1]

Step 1: This step was performed in the same manner as step 1 of Example 24.
Step 2: This step was performed in the same manner as step 2 of Example 24.
Step 3: This step was performed in the same manner as step 3 of Example 24, except that 2,4-dimethoxyaniline (40 mg, 0.261 mM) was used instead of 3-fluoropyridin-2-amine as the nucleophilic reagent, thereby obtaining the desired compound (5ad) (60 mg, 49%).

Brown solid, Rf 0.3 (Ethyl Acetate:n-Hexane=1:4); 1H-NMR (DMSO, 500 MHz) δ 10.76 (s, 1H), 8.0 (d, 1H, J=8.7 Hz), 7.7 (d, 1H J=15.0 Hz), 6.6 (d, 1H, J=2.5 Hz), 6.58 (d, 1H, J=7.8 Hz), 6.6 (dd, 1H, J=2.5 Hz, 11.0 Hz), 6.5 (d, 1H, J=2.5 Hz), 3.74 (s, 3H), 3.65 (s, 3H); LC-MS [M+H]+ 467.

Example 30

Preparation of KCH-1539

N-((4-(benzyloxy)phenyl)carbamoyl)-2-(3,5-bis(trifluoromethyl)phenoxy) acetamide (5ae)

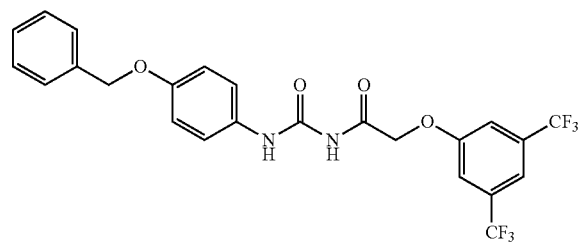 [SMILES: O=C(COc1cc(C(F)(F)F)cc(C(F)(F)F)c1)NC(=O)Nc1ccc(OCc2ccccc2)cc1]

Step 1: This step was performed in the same manner as step 1 of Example 24.
Step 2: This step was performed in the same manner as step 2 of Example 24.
Step 3: This step was performed in the same manner as step 3 of Example 24, except that 4-(benzyloxy)aniline HCl (61 mg, 0.260 mM) was used instead of 3-fluoropyridin-2-amine as the nucleophilic reagent, thereby obtaining the desired compound (5ae) (32 mg, 24%).

Brown solid, Rf 0.3 (Ethyl Acetate:n-Hexane=1:4); 1H-NMR (DMSO, 500 MHz) δ 10.65 (s, 1H), 9.93 (s, 1H), 7.72 (s, 2H), 7.68 (s, 1H), 7.44-7.37 (m, 5H), 7.33-7.30 (m, 2H), 5.1 (d, 2H, J=7.0 Hz), 3.2 (d, 2H); LC-MS [M+Na]+ 536.

Example 31

Preparation of KCH-1540

2-(3,5-bis(trifluoromethyl)phenoxy)-N-((2-fluorophenyl)carbamoyl)acetamide (5af)

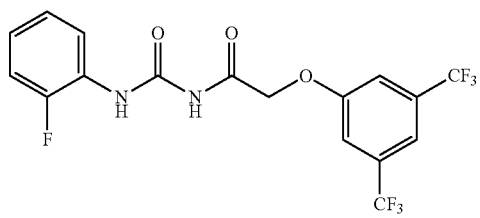 [SMILES: O=C(COc1cc(C(F)(F)F)cc(C(F)(F)F)c1)NC(=O)Nc1ccccc1F]

Step 1: This step was performed in the same manner as step 1 of Example 24.

Step 2: This step was performed in the same manner as step 2 of Example 24.

Step 3: This step was performed in the same manner as step 3 of Example 24, except that 2-fluoroaniline (0.025 ml, 0.260 mM) was used instead of 3-fluoropyridin-2-amine as the nucleophilic reagent, thereby obtaining the desired compound (5af) (84 mg, 76%).

White solid, Rf 0.3 (Ethyl Acetate:n-Hexane=1:4); 1H-NMR (DMSO, 500 MHz) δ 10.96 (s, 1H), 10.36 (s, 1H), 8.20 (t, 1H, J=9.8 Hz), 7.73 (s, 2H), 7.69 (s, 1H), 7.33 (t, 1H, J=9.8 Hz), 7.2 (t, 1H, J=7.6 Hz), 7.15-7.11 (m, 1H), 5.10 (s, 2H); LC-MS [M+Na]+447.

Example 32

Preparation of KCH-1541

N-((4-bromo-3-methoxyphenyl)carbamoyl)-2-(3-bromophenoxy)acetamide (5ag)

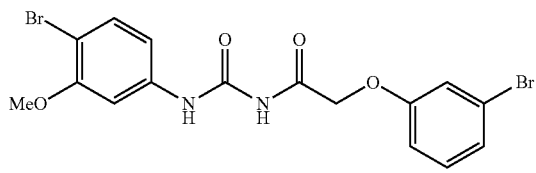 [SMILES: COc1cc(NC(=O)NC(=O)COc2cccc(Br)c2)ccc1Br]

Step 1: The process described in step 1 of Preparation Example 1 was performed using 3-bromophenol as a nucleophilic reagent.

Step 2: This step was performed in the same manner as step 2 of Example 1, except that 2-(3-bromophenoxy)acetamide (2ag) (36 mg, 0.158 mM) obtained in step 1 was used instead of 2-(5-phenyl-2H-tetrazol-2-yl)acetamide (2a).

Step 3: This step was performed in the same manner as step 3 of Example 1, except that 2-(3-bromophenoxy)acetyl isocyanate (3ag) obtained in step 2 was used instead of 2-(5-phenyl-2H-tetrazol-2-yl)acetyl isocyanate (3a), and 4-bromo-3-methoxyaniline (1 equivalent) (27 mg, 0.243 mM) was used instead of 4-bromo-3-methoxyaniline as the nucleophilic reagent, thereby obtaining the desired compound (5ag) (84 mg, 76%).

White solid, Rf 0.4 (Ethyl Acetate:n-Hexane=1:4); 1H-NMR (DMSO, 500 MHz) δ 10.73 (s, 1H), 10.34 (s, 1H), 7.98 (d, 1H, J=9.3 Hz), 7.29-7.16 (m, 3H), 6.98 (dd, 1H, J=1.5 Hz, 10.0 Hz), 6.64 (d, 1H, J=3.0 Hz), 6.50 (dd, 1H, J=2.3 Hz, 11.0 Hz), 4.83 (s, 2H), 3.82 (s, 3H).

Example 33

Preparation of KCH-1542

2-(3-bromophenoxy)-N-((2,4-dimethoxyphenyl)carbamoyl)acetamide (5ah)

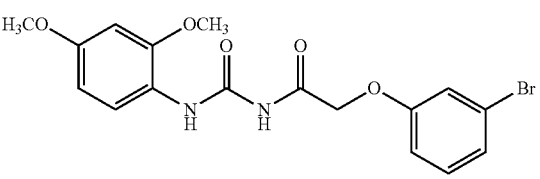 [SMILES: COc1ccc(NC(=O)NC(=O)COc2cccc(Br)c2)c(OC)c1]

Step 1: This step was performed in the same manner as step 1 of Example 32.

Step 2: This step was performed in the same manner as step 2 of Example 32.

Step 3: This step was performed in the same manner as step 3 of Example 32, except that 2,4-dimethoxyaniline (1 equivalent) (0.025 ml, 0.260 mM) was used instead of 4-bromo-3-methoxyaniline as the nucleophilic reagent, thereby obtaining the desired compound (5ah) (52 mg, 49%).

Yellow solid, Rf 0.25 (Ethyl Acetate:n-Hexane=1:4); 1H-NMR (DMSO, 500 MHz) δ 10.19 (s, 1H), 7.5 (d, 2H, J=8.5 Hz), 7.30-7.17 (m, 4H), 7.0 (dd, 1H, J=2.3 Hz, 10.5 Hz), 5.75 (s, 2H), 3.81 (s, 3H); LC-MS [M+H]+409.

Example 34

Preparation of KCH-1420

2-(2,3-dimethylphenoxy)-N-((2-fluorophenyl)carbamoyl)acetamide (5aj)

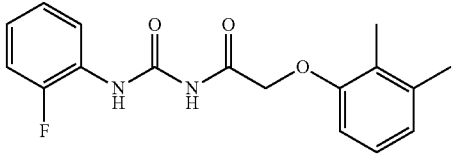 [SMILES: Cc1cccc(OCC(=O)NC(=O)Nc2ccccc2F)c1C]

Step 1: Preparation of 2-(2,3-dimethylphenoxy)acetamide

The process described in step 1 of Preparation Example 1 was performed using 2,3-dimethylphenol as a nucleophilic reagent.

Step 2: Preparation of 2-(2,3-dimethylphenoxy)acetyl isocyanate

This step was performed in the same manner as step 2 of Example 1, except that 2-(3,5-dimethylphenoxy)acetamide (2aj) (50 mg, 0.279 mM) obtained in step 1 was used instead of 2-(5-phenyl-2H-tetrazol-2-yl)acetamide (2a).

Step 3: Preparation of 2-(2,3-dimethylphenoxy)-N-((2-fluorophenyl)carbamoyl)acetamide This step was performed in the same manner as step 3 of Example 1, except that 2-(2,3-dimethylphenoxy)acetyl isocyanate) (3aj) obtained in step 2 was used instead of 2-(5-phenyl-2H-tetrazol-2-yl)acetyl isocyanate (3a), and 2-fluoroaniline (1 equivalent) (0.0224 ml, 0.233 mM) was used instead of 4-bromo-3-methoxyaniline as the nucleophilic reagent, thereby obtaining the desired compound (5aj) (44.2 mg, 50%).

White solid, Rf 0.3 (Ethyl Acetate:n-Hexane=1:4); 1H-NMR (DMSO, 500 MHz) δ 10.95 (s, 1H), 10.49 (s, 1H), 8.12 (t, 1H, J=9.7 Hz), 7.30 (m, 1H), 7.20 (t, 1H, J=7.0 Hz), 7.13 (m, 1H), 7.03 (t, 1H, J=8.0 Hz), 6.80 (d, 1H, J=7.7 Hz, 6.68 (d, 1H, J=8.3 Hz), 4.82 (s, 2H), 2.23 (s, 3H), 2.14 (s, 3H).

Example 35

Preparation of KCH-1421

2-(4-(benzyl oxy)phenoxy)-N-((2-fluorophenyl)carbamoyl)acetamide (5 ak)

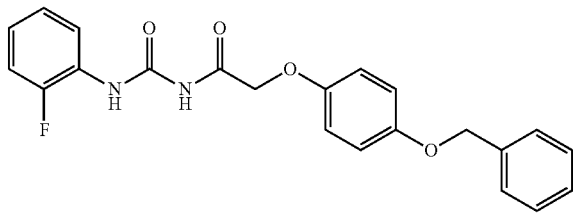 [SMILES: O=C(COc1ccc(OCc2ccccc2)cc1)NC(=O)Nc1ccccc1F]

Step 1: Preparation of 2-(4-(benzyloxy)phenoxy)acetamide

The process described in step 1 of Preparation Example 1 was performed using 4-(benzyloxy)phenol as a nucleophilic reagent.

Step 2: Preparation of 2-(4-(benzyloxy)phenoxy)acetyl isocyanate

This step was performed in the same manner as step 2 of Example 1, except that 2-(4-(benzyloxy)phenoxy)acetamide (2ak) (50 mg, 0.194 mM) obtained in step 1 was used instead of 2-(5-phenyl-2H-tetrazol-2-yl)acetamide (2a).

Step 3: Preparation of 2-(4-(benzyloxy)phenoxy)-N-((2-fluorophenyl)carbamoyl)acetamide This step was performed in the same manner as step 3 of Example 1, except that 2-(4-(benzyloxy)phenoxy)acetyl isocyanate (3ak) obtained in step 2 was used instead of 2-(5-phenyl-2H-tetrazol-2-yl)acetyl isocyanate (3a), and 2-fluoroaniline (1 equivalent) (0.0156 ml, 0.162 mM) was used instead of 4-bromo-3-methoxyaniline as the nucleophilic reagent, thereby obtaining the desired compound (5ak) (27.6 mg, 36%).

White solid, Rf 0.3 (Ethyl Acetate:n-Hexane=1:3); 1H-NMR (DMSO, 500 MHz) δ 10.92 (s, 1H), 10.50 (s, 1H), 8.13 (t, 1H, J=8.3 Hz), 7.43 (d, 2H), 7.38 (t, 2H, J=7.3 Hz), 7.33-7.28 (m, 2H), 7.20 (t, 1H, J=7.3 Hz), 7.13 (m, 1H), 6.96-6.94 (m, 2H), 6.91-6.89 (m, 2H), 5.04 (s, 2H), 4.75 (s, 2H).

Example 36

Preparation of KCH-1424, tert-butyl 4-(2-(3-(2-fluorophenyl)ureido)-2-oxoethyl)piperazine-1-carboxylate (5am)

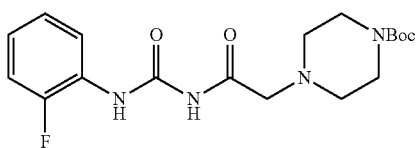 [SMILES: CC(C)(C)OC(=O)N1CCN(CC(=O)NC(=O)Nc2ccccc2F)CC1]

Step 1: This step was performed in the same manner as step 1 of Example 33.

Step 2: This step was performed in the same manner as step 2 of Example 33.

Step 3: Preparation of tert-butyl 4-(2-(3-(2-fluorophenyl)ureido)-2-oxoethyl)piperazine-1-carboxylate Tert-butyl piperazine-1-carboxylate (1 equivalent)(162 mg, 0.867 mM) was added to the compound (2-chloro-N-((2-fluorophenyl)carbamoyl)acetamide)(1 equivalent)(200 mg, 0.867 mM) obtained in step 2, and then the reactor was set to 80° C., after which methanol (6 ml) was added and the solution was stirred for 4 hours. The reaction was terminated by addition of H₂O to the reaction solution, and the reaction solution was extracted with ethyl acetate. The organic layer was dried with MgSO₄, filtered, and then concentrated under reduced pressure. The concentrated compound was subjected to column chromatography with Ethyl acetate:Hexane (1:1) to obtain the desired compound tert-butyl 4-(2-(3-(2-fluorophenyl)ureido)-2-oxoethyl) piperazine-1-carboxylate (122 mg, 37%).

Yellow solid, Rf 0.3 (Ethyl Acetate:n-Hexane=1:2); 1H-NMR (CDCl₃, 500 MHz) δ 10.57 (s, 1H), 9.26 (s, 1H), 8.19 (t, 1H, J=7.5 Hz), 7.15-7.05 (m, 3H), 3.53 (s, 4H), 3.23 (s, 2H), 2.58 (s, 4H), 1.48 (s, 6H).

Example 37

Preparation of KCH-1425

N-((2-fluorophenyl)carbamoyl)-2-morpholinoacetamide (5am)

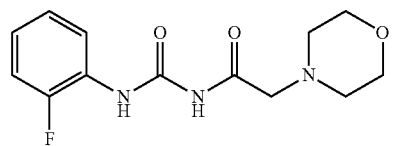 [SMILES: O=C(CN1CCOCC1)NC(=O)Nc1ccccc1F]

Step 1: The process described in step 1 of Preparation Example 2 was performed.

Step 2: The process described in step 2 of Preparation Example 2 was performed using 2-Fluoroaniline as a nucleophilic reagent.

Step 3: Methanol (4 ml) was added to the compound (2-chloro-N-((2-fluorophenyl)carbamoyl)acetamide)(1 equivalent)(191 mg, 0.830 mM) obtained in step 2, and then the reactor was set to 80° C., after which morpholine (3 equivalents) (217 mg, 2.49 mM) was added and the solution was stirred for 30 minutes. The reaction solution was stirred overnight at room temperature. The reaction was terminated by addition of $H_2O$ to the reaction solution, and the reaction solution was extracted with ethyl acetate. The organic layer was dried with $MgSO_4$, filtered, and then concentrated under reduced pressure. The concentrated compound was subjected to column chromatography with Ethyl acetate:Hexane (1:2) to obtain the desired compound N-((2-fluorophenyl)carbamoyl)-2-morpholinoacetamide)(124 mg, 53%).

White solid, Rf 0.3 (Ethyl Acetate:n-Hexane=1:2); 1H-NMR ($CDCl_3$, 500 MHz) δ 10.59 (s, 1H), 9.25 (s, 1H), 8.20 (t, 1H, J=7.6 Hz), 7.16-7.05 (m, 3H), 3.79 (t, 4H, J=4.5 Hz), 3.20 (s, 2H), 2.62 (t, 4H, J=4.8 Hz).

Example 38

Screening of Talin Antagonist Candidates

Platelets bind to fibrinogen present in blood and produce thrombi. This binding is mediated by integrin αIIbβ3 present in the platelet cell membrane, and this integrin binds to fibrinogen after being activated by talin. In order to enable high-throughput efficacy testing by simplifying this procedure into a cell line-based experiment, integrin αIIbβ3 was first stably expressed in the CHO cell line using lentivirus, thereby constructing a CHO/αIIbβ3 cell line. The constructed cell line was cultured in a fibrinogen-coated 96-well plate for 1 hour and washed, after which the amount of remaining cells was measured to evaluate the efficacy of a talin antagonist candidate. In this procedure, in order to measure the relative amount of the CHO/αIIbβ3 cell line remaining in the well due to binding to fibrinogen, a cell counting kit-8 (CCK-8) was used to measure the activity of dehydrogenase present in the remaining cells. When the activity of dehydrogenase appeared due to the presence of the cells, the color of CCK-8 changed from yellow to orange (FIG. 1). To measure the degree to which the color changed to orange, the absorbance at a wavelength of 450 nm was measured with a plate reader. This enabled easy, fast and reliable high-throughput screening.

To screen talin antagonist candidates, inhibition of the binding affinity between the CHO/αIIbβ3 cell line and fibrinogen was examined by the above-described efficacy testing method.

Figure 2:
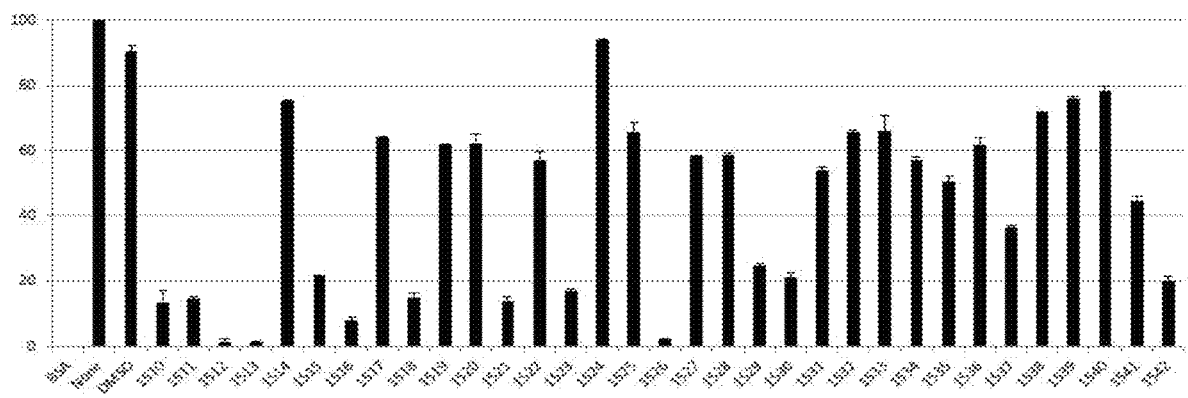
FIG. 2 shows the results of screening thrombosis inhibitory candidates according to Example 38 of the present invention. Cells expressing platelet integrin αIIbβ3 were incubated with 0.2 mM of candidates, and the binding between the cells and fibrinogen was verified according to the experimental method shown in FIG. 1.
Figure 2:
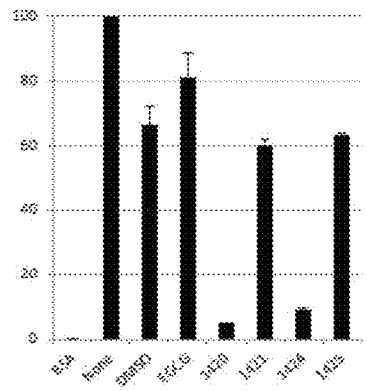
Figure 3:
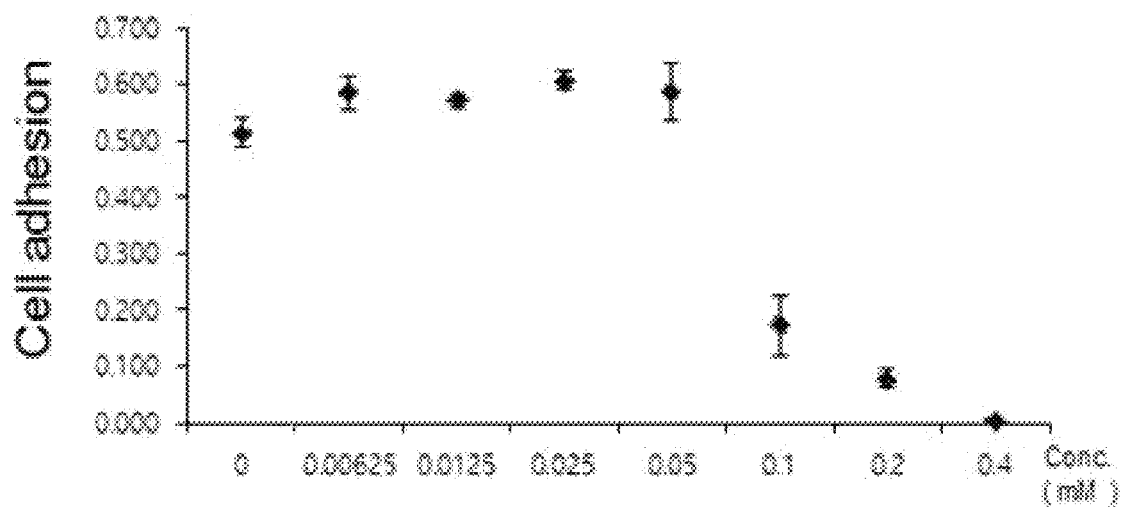
FIG. 3 shows the results of testing the concentration-dependent inhibitory activity of effective representative thrombosis inhibitory candidates in Example 38 of the present invention.
Figure 3:
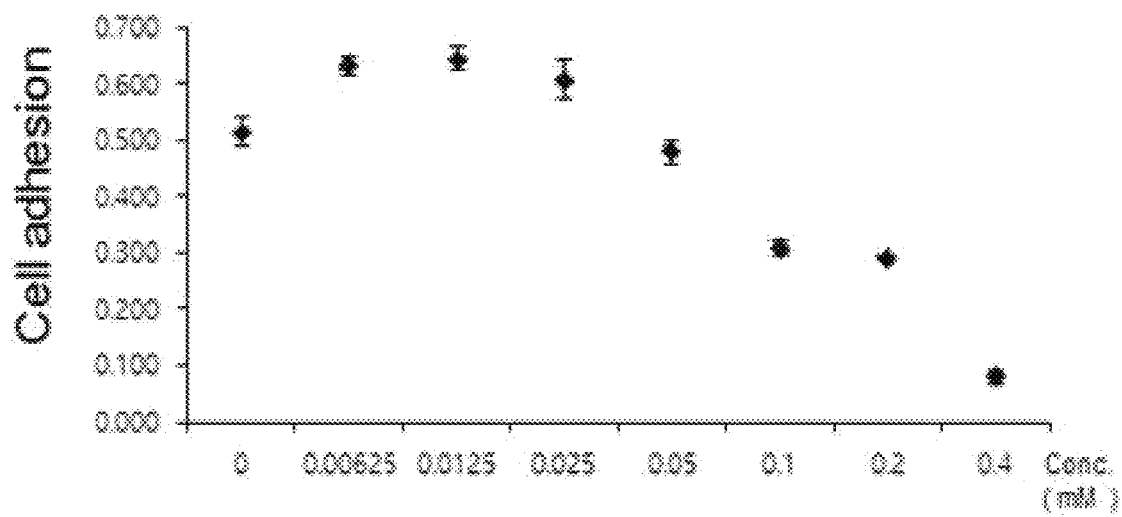

As a result, it was shown that compounds, including KCH-1420, KCH-1424, KCH-1510, KCH-1511, KCH-1512, KCH-1513, KCH-1516, KCH-1518, KCH-1521, KCH-1523, KCH-1526, KCH-1529, KCH-1530, and KCH-1542 inhibited the binding between the CHO/αIIbβ3 cell line and fibrinogen by at least 80% compared to a negative control (FIG. 2). FIG. 3 shows the concentration-dependent effects of KCH-1513 and KCH-1521 on inhibition of the binding between the CHO/αIIbβ3 cell line and fibrinogen. In FIG. 3, like FIG. 2, cells expressing platelet integrin αIIbβ3 were incubated with varying concentrations of a candidate, and the binding between the cells and fibrinogen was examined. Cell adhesion on the Y-axis is the relative degree of cell-fibrinogen binding. KCH-1513 and KCH-1521 showed an inhibitory effect of at least 50% at a concentration ranging from 0.02 to 0.07 mM.

Example 39

Measurement of Binding Affinity between Talin Protein and Talin Antagonist Candidate To measure the binding affinity between the talin protein and a talin antagonist candidate, surface plasmon resonance spectroscopy was used. Specifically, a talin antagonist candidate was added to the talin protein immobilized on a sensor chip, and the affinity constant between the two substances was measured by surface plasmon resonance (hereinafter referred to as 'SPR') spectrometry.

Talin is divided into an N-terminal head domain and a C-terminal rod domain, and the head domain is further divided into four subdomains, F0, F1, F2 and F3. Among them, F3 is known as an integrin binding site. Thus, 6×His-tagged F2F3 protein containing F3 was isolated and purified. As a sensor chip for immobilizing the talin protein, HTEPBE10PO1 (Biorad) was used. SPR was measured using ProteON™ XPR36 (Biorad).

Figure 4:
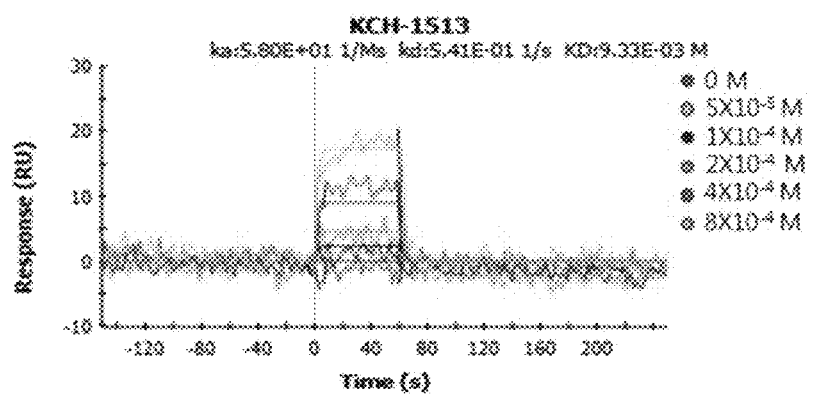
FIG. 4 shows the results of measuring the binding affinity of talin antagonist candidates for talin protein by surface plasmon resonance spectroscopy in Example 39 of the present invention.
Figure 4:
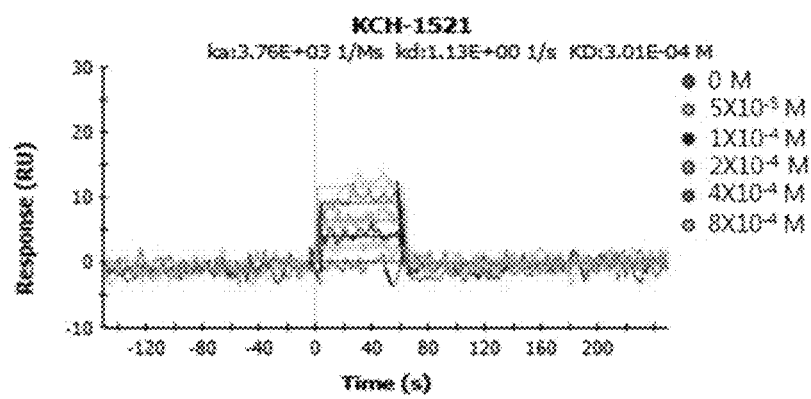

As a result, as shown in FIG. 4, the compounds KCH-1513 and KCH-1521 were measured to have affinity constants of $9.33 \times 10^{-3}$ M and $2.71 \times 10^{-4}$ M, respectively, and it was shown that the talin antagonist candidates did bind to the talin protein in a concentration-dependent manner.

Example 40

Evaluation of Platelet Aggregation Inhibitory Effect Using Mouse Platelets

Figure 5:
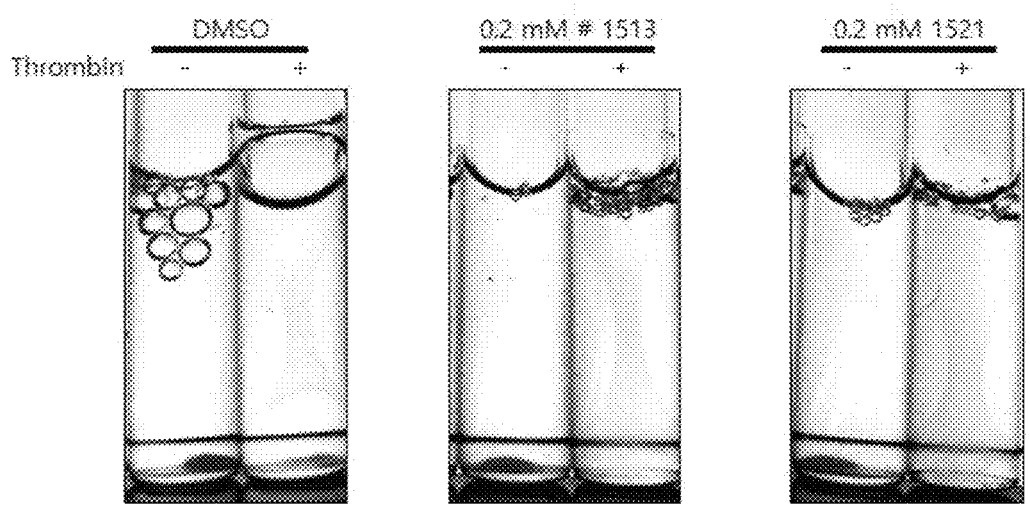
FIG. 5 shows the results of analyzing the platelet aggregation inhibitory effects of KCH-1513 and KCH-1521 in Example 40 of the present invention.

In order to examine whether platelet aggregation is actually inhibited by the compound KCH-1513 or KCH-1521, this test was performed. It is well known that platelets bind to fibrinogen in blood and form thrombi, which leads to the contraction of intracellular skeletal muscle due to signaling after the binding between activated integrin a αIIbβ3 and fibrinogen. To achieve this thrombus formation in vitro, mouse blood platelets were isolated and thrombin known as a platelet activator was added thereto. As a result, as shown in the left photograph of FIG. 5, the platelets were aggregated. However, when platelets were treated with thrombin in combination with KCH-1513 or KCH-1521, it was observed that platelet aggregation that was increased by thrombin decreased when 0.2 mM of KCH-1513 (middle photograph) or the same concentration of KCH-1521 (right photograph) was added. This suggests that the KCH-1513 and KCH-1521 compounds of the present invention significantly inhibit platelet aggregation as shown in FIG. 5.

Example 41

Figure 6:
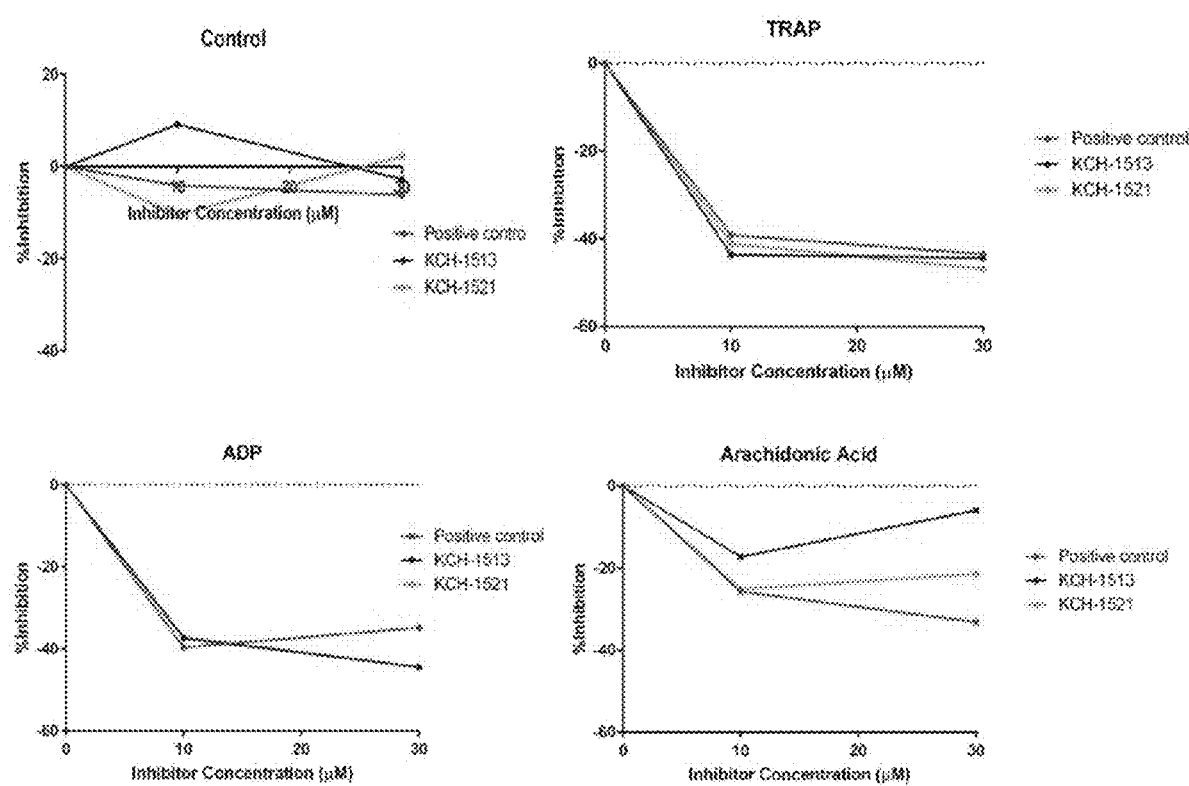
FIG. 6 depicts graphs showing the results obtained by treating human peripheral blood with platelet aggregation agonists (TRAP, ADP and arachidonic acid), and then treating the blood again with compounds of the present invention, and comparing and quantifying the inhibition of platelet aggregation, in Example 41 of the present invention in order to compare the platelet aggregation inhibitory activities of various compounds in human peripheral blood.

Comparison of Platelet Aggregation Inhibitory Activity Using Human Peripheral Blood Platelets isolated from human peripheral blood were treated with TRAP (32 μM), ADP (6.5 μM) and arachidonic acid (AA; 0.5 mM), which are platelet aggregation agonists, in combination with different concentrations (0 μM, 10 μM and 30 μM) of various compounds (KCH-1513 and KCH-1521), and inhibition of aggregation of the platelets was compared (FIG. 6). As a result, it could be seen that KCH-1513 and KCH-1521 had platelet aggregation inhibitory activities similar to that of a positive control.

Example 42

Figure 8:
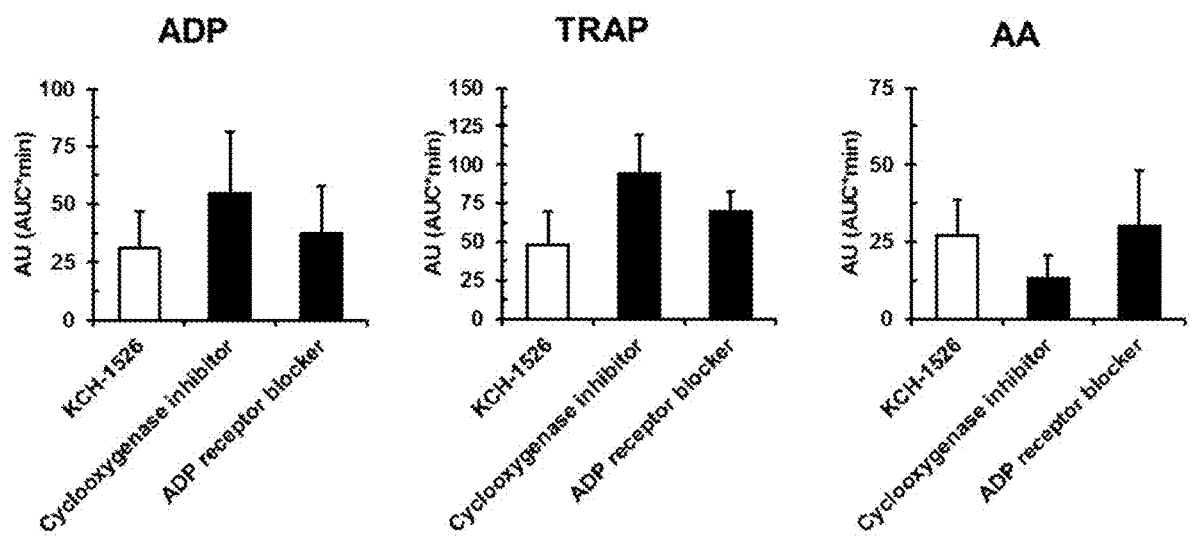
FIG. 8 depicts graphs showing the results obtained by treating human peripheral blood (which has been administered with conventional platelet inhibitors) with platelet aggregation agonists (TRAP, ADP and arachidonic acid), and then treating the blood again with compounds of the present invention, and comparing and quantifying the inhibition of platelet aggregation, in Example 42 of the present invention in order to compare the platelet aggregation inhibitory activities of various compounds in human peripheral blood.

Comparison of Platelet Aggregation Inhibitory Activity Using Human Peripheral Blood Platelets isolated from human peripheral blood, which has been administered with conventional platelet inhibitors (cyclooxygenase inhibitor and ADP receptor blocker), were treated with ADP (6.5 μM), TRAP (32 μM) and arachidonic acid (AA; 0.5 mM), which are platelet aggregation agonists, in combination with KCH-1526, and inhibition of aggregation of the platelets was compared (FIG. 8). As a result, it could be seen that treatment with the representative novel compound KCH-1526 exhibited similar or better platelet aggregation inhibitory activity than those of the conventional platelet inhibitors (cyclooxygenase inhibitor and ADP receptor blocker) in the platelets treated with the platelet aggregation agonists (ADP, TRAP and arachidonic acid).

FORMULATION EXAMPLES

Hereinafter, formulations which may be prepared as pharmaceutical compositions of the present invention will be illustrated.

Formulation Example 1

Preparation of Pharmaceutical Formulation for Oral or Parenteral Administration

1. Preparation of Powder Formulation
N-acylurea derivative: 2 g;
Lactose: 1 g
The above components were mixed with each other and filled into an airtight bag, thereby preparing a powder formulation.
2. Preparation of Tablet Formulation
N-acylurea derivative: 100 mg;
Corn starch: 100 mg;
Lactose: 100 mg;
Magnesium stearate: 2 mg.
The above components were mixed with one another and compressed into a tablet according to a conventional tablet preparation method, thereby preparing a tablet formulation.
3. Preparation of Capsule Formulation
N-acylurea derivative: 100 mg;
Corn starch: 100 mg;
Lactose: 100 mg;
Magnesium stearate: 2 mg.
The above components were mixed with one another and filled into a gelatin capsule according to a conventional capsule preparation method, thereby preparing a capsule formulation.
4. Preparation of Injectable Formulation
N-acylurea: 10 µg/ml;
Dilute hydrochloric acid BP: to pH 3.5;
Sodium chloride BP for injection: to 1 ml.
A 2-ethoxypropionic acid derivative was dissolved in a suitable volume of sodium chloride BP for injection, the pH of the resultant solution was adjusted to pH3.5 with dilute hydrochloric acid BP, and then the solution was made to volume with sodium chloride BP for injection and thoroughly mixed. The solution was filled into 5 ml type I clear glass ampoules which were then sealed under a headspace of air by fusion of the glass, and then sterilized by autoclaving at 120° C. for not less than 15 minutes, thereby preparing an injectable liquid formulation.

INDUSTRIAL APPLICABILITY

The N-acylurea derivative according to the present invention can inhibit platelet aggregation by inhibiting the activity of talin in the intracellular matrix, and thus can be useful for the prevention or treatment of cardiovascular disease.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:
1. A compound or a pharmaceutically acceptable salt thereof, wherein the compound is selected from the group consisting of:
(1) N-((4-bromo-3-methoxyphenyl) carbamoyl)-2-(5-phenyl-2H-tetrazol-2-yl)acetamide

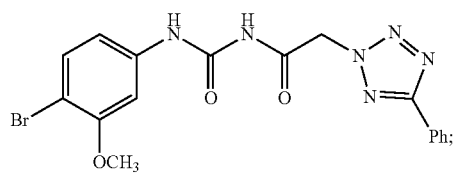 [SMILES: COc1cc(NC(=O)NC(=O)Cn2nnc(-c3ccccc3)n2)ccc1Br]

(2) N-((4-phenoxyphenyl)carbamoyl)-2-(5-phenyl-2H-tetrazol-2-yl)acetamide

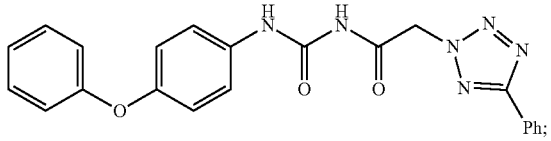 [SMILES: O=C(Cn1nnc(-c2ccccc2)n1)NC(=O)Nc1ccc(Oc2ccccc2)cc1]

(3) N-((4-methoxybenzyl)carbamoyl)-2-(5-phenyl-2H-tetrazol-2-yl)acetamide

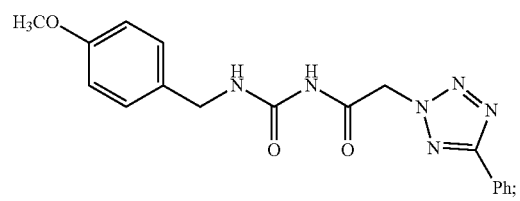 [SMILES: COc1ccc(CNC(=O)NC(=O)Cn2nnc(-c3ccccc3)n2)cc1]

(4) N-((2-(3a,7a-dihydro-1H-indol-3-yl)ethyl)carbamoyl)-2-(5-phenyl-2H-tetrazol-2-yl)acetamide)

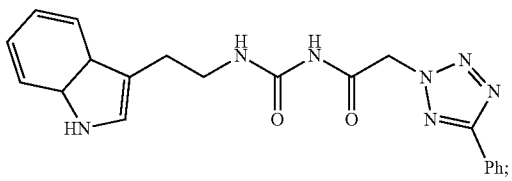 [SMILES: O=C(Cn1nnc(-c2ccccc2)n1)NC(=O)NCCC1=CNC2C=CC=CC12]

(5) N-((2,4-dimethoxyphenyl)carbamoyl)-2-(5-phenyl-2H-tetrazol-2-yl)acetamide

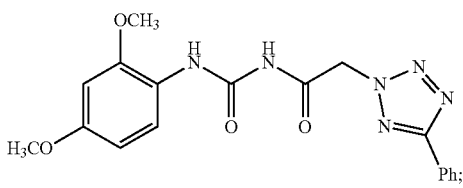 [SMILES: COc1ccc(NC(=O)NC(=O)Cn2nnc(-c3ccccc3)n2)c(OC)c1]

(6) N-((4-(benzyloxy)phenyl)carbamoyl)-2-(5-phenyl-2H-tetrazol-2-yl)acetamide

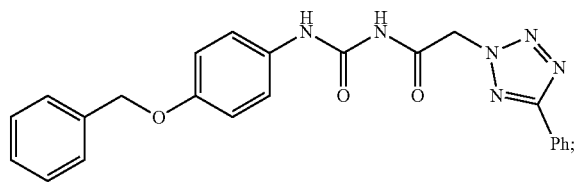 [SMILES: O=C(Cn1nnc(-c2ccccc2)n1)NC(=O)Nc1ccc(OCc2ccccc2)cc1]

(7) N-((2-fluorophenyl)carbamoyl)-2-(5-phenyl-2H-tetrazol-2-yl)acetamide

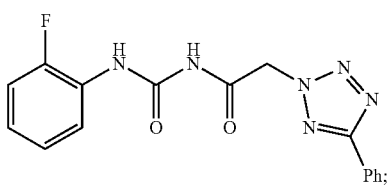 [SMILES: O=C(Cn1nnc(-c2ccccc2)n1)NC(=O)Nc1ccccc1F]

(8) 2-(benzo[d][1,3]dioxol-5-yloxy)-N-((3-fluoropyridin-2-yl)carbamoyl)acetamide

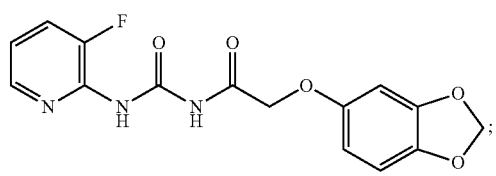 [SMILES: O=C(COc1ccc2c(c1)OCO2)NC(=O)Nc1ncccc1F]

(9) 2-(benzo[d][1,3]dioxol-5-yloxy)-N-((4-bromo-3-methoxyphenyl)carbamoyl)acetamide

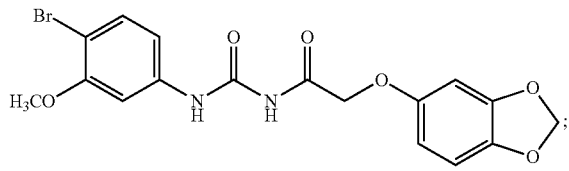 [SMILES: COc1cc(NC(=O)NC(=O)COc2ccc3c(c2)OCO3)ccc1Br]

(10) 2-(benzo[d][1,3]dioxol-5-yloxy)-N-((4-phenoxyphenyl)carbamoyl)acetamide

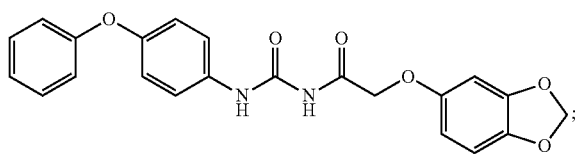 [SMILES: O=C(COc1ccc2c(c1)OCO2)NC(=O)Nc1ccc(Oc2ccccc2)cc1]

(11) 2-(benzo[d][1,3]dioxol-5-yloxy)-N-((4-methoxybenzyl)carbamoyl)acetamide

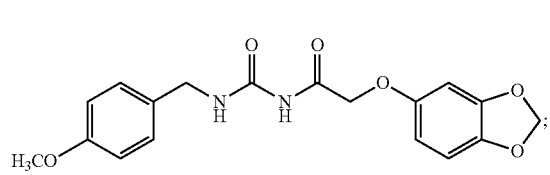 [SMILES: COc1ccc(CNC(=O)NC(=O)COc2ccc3c(c2)OCO3)cc1]

(12) N-((2-(1H-indol-3-yl)ethyl)carbamoyl)-2-(benzo[d][1,3]dioxol-5-yloxy)acetamide

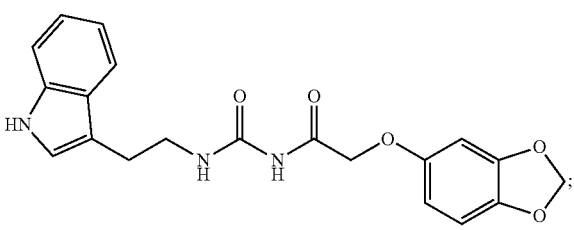 [SMILES: O=C(COc1ccc2c(c1)OCO2)NC(=O)NCCc1c[nH]c2ccccc12]

(13) 2-(benzo[d][1,3]dioxol-5-yloxy)-N-((2,4-dimethoxyphenyl)carbamoyl)acetamide

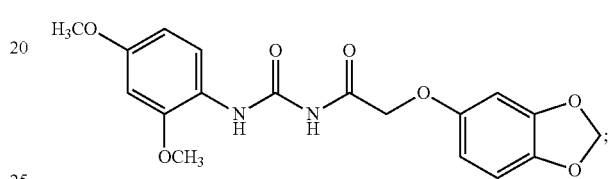

(14) 2-(benzo[d][1,3]dioxol-5-yloxy)-N-((4-(benzyloxy)phenyl)carbamoyl)acetamide

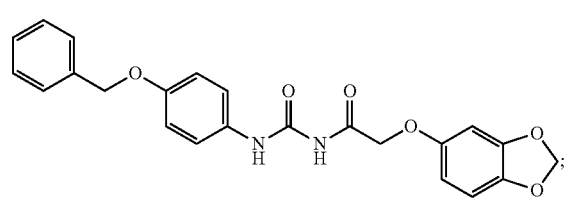 [SMILES: O=C(COc1ccc2c(c1)OCO2)NC(=O)Nc1ccc(OCc2ccccc2)cc1]

(15) 2-(benzo[d][1,3]dioxol-5-yloxy)-N-((2-fluorophenyl)carbamoyl)acetamide

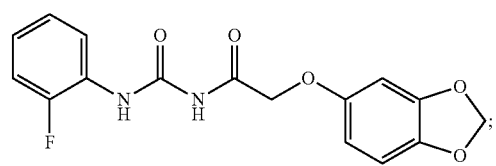 [SMILES: O=C(COc1ccc2c(c1)OCO2)NC(=O)Nc1ccccc1F]

(16) N-((3-fluoropyridin-2-yl)carbamoyl)-2-(2-methoxyphenoxy)acetamide

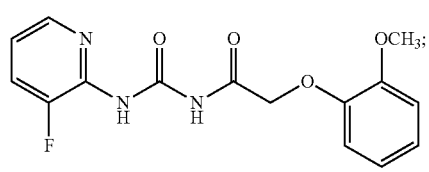 [SMILES: COc1ccccc1OCC(=O)NC(=O)Nc1ncccc1F]

(17) N-((4-bromo-3-methoxyphenyl)carbamoyl)-2-(2-methoxyphenoxy)acetamide

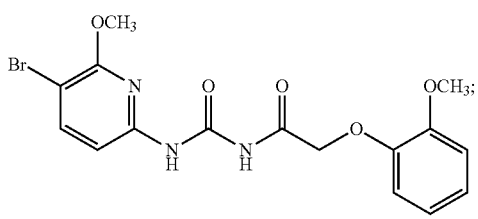

(18) 2-(2-methoxyphenoxy)-N-((4-phenoxyphenyl)carbamoyl)acetamide

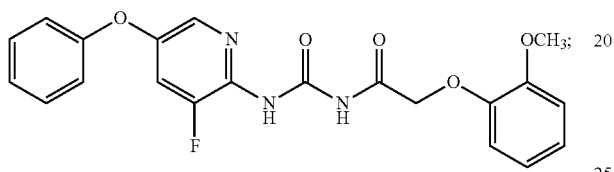

(19) N-((4-methoxybenzyl)carbamoyl)-2-(2-methoxyphenoxy)acetamide

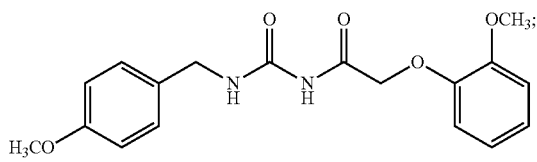 [SMILES: COc1ccc(CNC(=O)NC(=O)COc2ccccc2OC)cc1]

(20) N-((2-(1H-indol-3-yl)ethyl)carbamoyl)-2-(2-methoxyphenoxy)acetamide

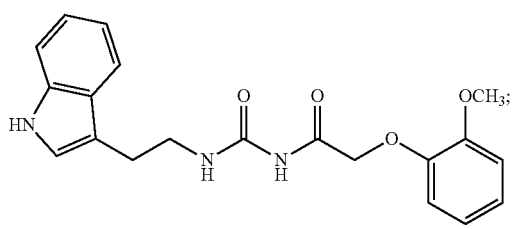 [SMILES: COc1ccccc1OCC(=O)NC(=O)NCCc1c[nH]c2ccccc12]

(21) N-((2,4-dimethoxyphenyl)carbamoyl)-2-(2-methoxyphenoxy)acetamide

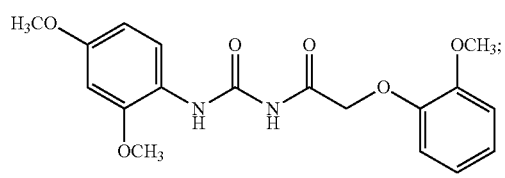 [SMILES: COc1ccc(NC(=O)NC(=O)COc2ccccc2OC)c(OC)c1]

(22) N-((4-(benzyloxy)phenyl)carbamoyl)-2-(2-methoxyphenoxy)acetamide

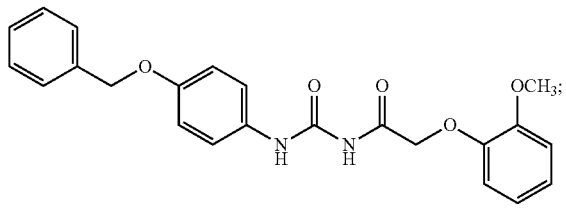 [SMILES: COc1ccccc1OCC(=O)NC(=O)Nc1ccc(OCc2ccccc2)cc1]

(23) 2-(3,5-bis(trifluoromethyl)phenoxy)-N-((3-fluoropyridin-2-yl)carbamoyl)acetamide

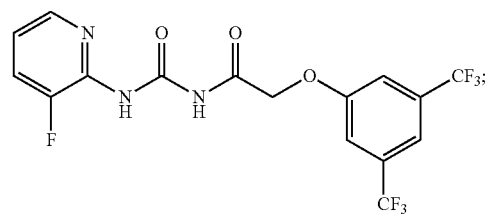

(24) 2-(3,5-bis(trifluoromethyl)phenoxy)-N-((4-bromo-3-methoxyphenyl)carbamoyl)-acetamide

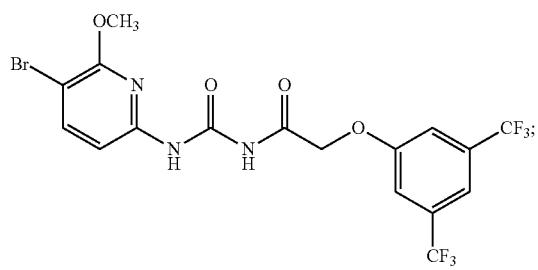 [SMILES: COc1nc(NC(=O)NC(=O)COc2cc(C(F)(F)F)cc(C(F)(F)F)c2)ccc1Br]

(25) 2-(3,5-bis(trifluoromethyl)phenoxy)-N-((4-methoxybenzyl)carbamoyl)acetamide

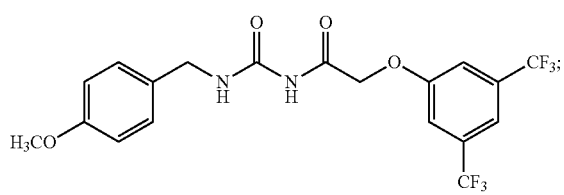 [SMILES: COc1ccc(CNC(=O)NC(=O)COc2cc(C(F)(F)F)cc(C(F)(F)F)c2)cc1]

(26) N-((2-(1H-indol-3-yl)ethyl)carbamoyl)-2-(3,5-bis(trifluoromethyl)phenoxy)acetamide

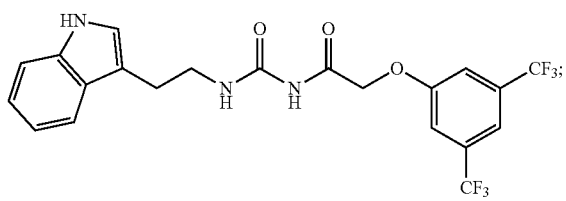 [SMILES: O=C(COc1cc(C(F)(F)F)cc(C(F)(F)F)c1)NC(=O)NCCc1c[nH]c2ccccc12]

(27) 2-(3,5-bis(trifluoromethyl)phenoxy)-N-((2,4-dimethoxyphenyl)carbamoyl)acetamide

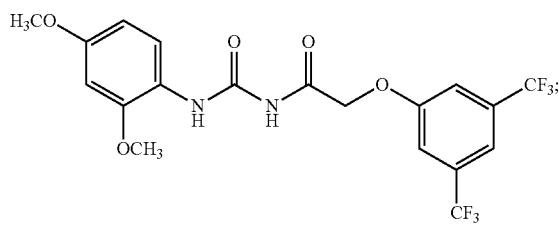 [SMILES: COc1ccc(NC(=O)NC(=O)COc2cc(C(F)(F)F)cc(C(F)(F)F)c2)c(OC)c1]

(28) N-((4-(benzyloxy)phenyl)carbamoyl)-2-(3,5-bis(trifluoromethyl)phenoxy)acetamide

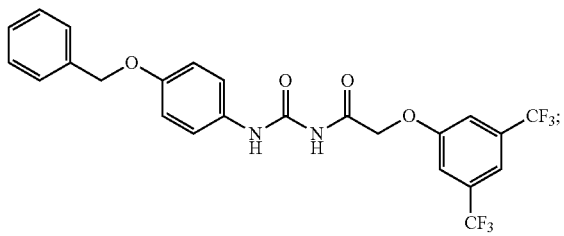 [SMILES: O=C(COc1cc(C(F)(F)F)cc(C(F)(F)F)c1)NC(=O)Nc1ccc(OCc2ccccc2)cc1]

(29) 2-(3,5-bis(trifluoromethyl)phenoxy)-N-((2-fluorophenyl)carbamoyl)acetamide

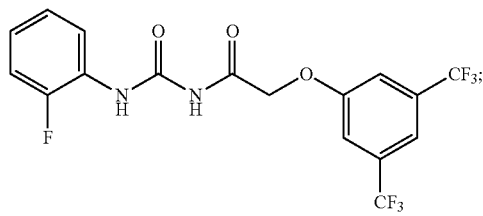 [SMILES: O=C(COc1cc(C(F)(F)F)cc(C(F)(F)F)c1)NC(=O)Nc1ccccc1F]

(30) N-((4-bromo-3-methoxyphenyl)carbamoyl)-2-(3-bromophenoxy)acetamide

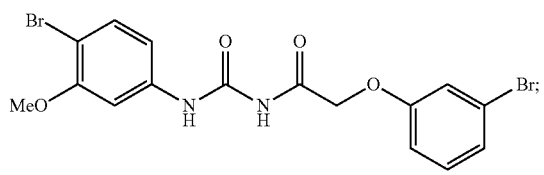 [SMILES: COc1cc(NC(=O)NC(=O)COc2cccc(Br)c2)ccc1Br]

(31) 2-(3-bromophenoxy)-N-((2,4-dimethoxyphenyl)carbamoyl)acetamide

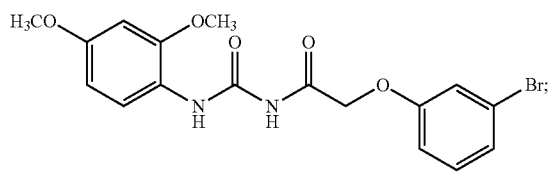 [SMILES: COc1ccc(NC(=O)NC(=O)COc2cccc(Br)c2)c(OC)c1]

(32) 2-(2,3-dimethylphenoxy)-N-((2-fluorophenyl)carbamoyl)acetamide

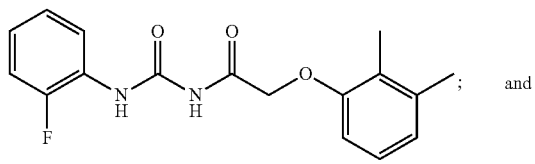 [SMILES: Cc1cccc(OCC(=O)NC(=O)Nc2ccccc2F)c1C]

(33) 2-(4-(benzyloxy)phenoxy)-N-((2-fluorophenyl)carbamoyl)acetamide

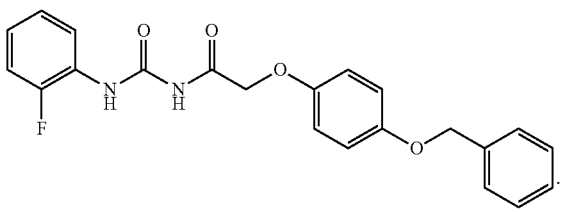 [SMILES: O=C(COc1ccc(OCc2ccccc2)cc1)NC(=O)Nc1ccccc1F]

2. The compound or the pharmaceutically acceptable salt thereof according to claim 1, wherein the compound is:
N-((2-(3a,7a-dihydro-1H-indol-3-yl)ethyl)carbamoyl)-2-(5-phenyl-2H-tetrazol-2-yl)acetamide)

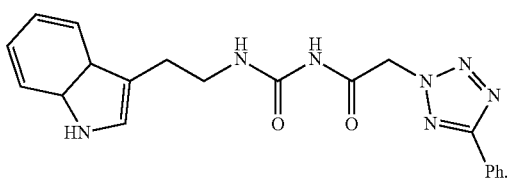 [SMILES: O=C(Cn1nnc(-c2ccccc2)n1)NC(=O)NCCC1=CNC2C=CC=CC12]

3. The compound or the pharmaceutically acceptable salt thereof according to claim 1, wherein the compound is:
N-((2-(1H-indol-3-yl)ethyl)carbamoyl)-2-(benzo[d][1,3]dioxol-5-yloxy)acetamide

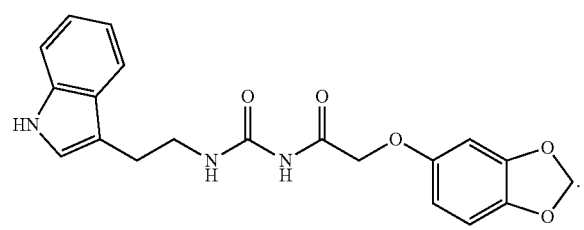 [SMILES: O=C(COc1ccc2c(c1)OCO2)NC(=O)NCCc1c[nH]c2ccccc12]

4. The compound or the pharmaceutically acceptable salt thereof according to claim 1, wherein the compound is:
N-((4-bromo-3-methoxyphenyl)carbamoyl)-2-(2-methoxyphenoxy)acetamide

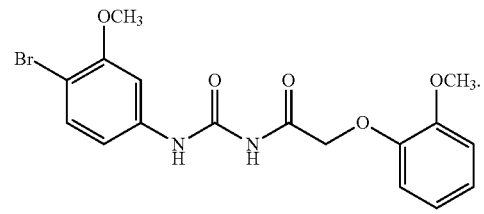

5. The compound or the pharmaceutically acceptable salt thereof according to claim 1, wherein the compound is:

2-(3-bromophenoxy)-N-((2,4-dimethoxyphenyl)carbamoyl)acetamide

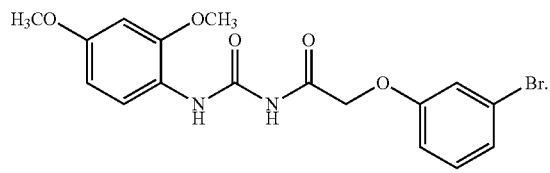 [SMILES: COc1ccc(NC(=O)NC(=O)COc2cccc(Br)c2)c(OC)c1]

6. A pharmaceutical composition for treating cardiovascular disease, comprising the compound or the pharmaceutically acceptable salt thereof of claim 1, as an active ingredient, and a pharmaceutically acceptable carrier.

7. The pharmaceutical composition of claim 6, wherein the cardiovascular disease is selected from the group consisting of hypertension, ischemic heart disease, coronary artery disease, angina pectoris, myocardial infarction, arteriosclerosis, cerebrovascular disease and arrhythmia.

8. A compound or a pharmaceutically acceptable salt thereof, wherein the compound is selected from the group consisting of (i)  N-((2-(3a,7a-dihydro-1H-indol-3-yl)ethyl)carbamoyl)-2-(5-phenyl-2H-tetrazol-2-yl)acetamide)

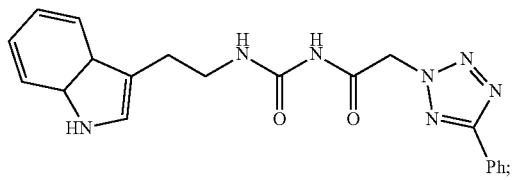 [SMILES: O=C(Cn1nnc(-c2ccccc2)n1)NC(=O)NCCC1=CNC2C=CC=CC12]

(ii)  N-((2-(1H-indol-3-yl)ethyl)carbamoyl)-2-(benzo[d][1,3]dioxol-5-yloxy)acetamide

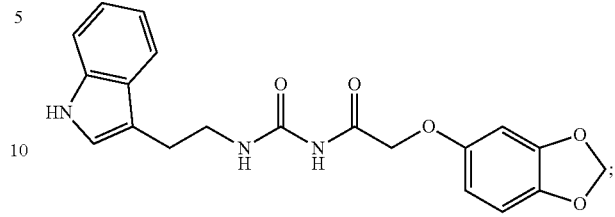

and (iii)  2-(3,5-bis(trifluoromethyl)phenoxy)-N-((2,4-dimethoxyphenyl)carbamoyl)acetamide

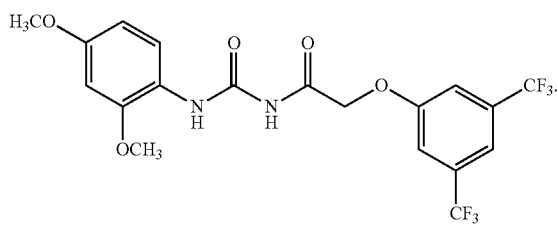 [SMILES: COc1ccc(NC(=O)NC(=O)COc2cc(C(F)(F)F)cc(C(F)(F)F)c2)c(OC)c1]

* * * * *

UNITED STATES PATENT AND TRADEMARK OFFICE
CERTIFICATE OF CORRECTION

PATENT NO. : 11,306,073 B2
APPLICATION NO. : 16/094826
DATED : April 19, 2022
INVENTOR(S) : Soon Jun Hong et al.

It is certified that error appears in the above-identified patent and that said Letters Patent is hereby corrected as shown below:

In the Specification

Column 7, Lines 42-43,
"2-(3,5-bis(tri fluoromethyl)phenoxy)-N-((4-methoxybenzyl)carbamoyl)acetamide" should be
-- 2-(3,5-bis(trifluoromethyl)phenoxy)-N-((4-methoxybenzyl)carbamoyl)acetamide --.

Column 16, Line 9, "($5_e$)" should be -- (5e) --.

Column 16, Line 43, "(5)" should be -- (5f) --.

Column 18, Lines 10-11,
"2-(benzo[d][1,3]dioxo1-5-yloxy)-N-((4-bromo-3-methoxyphenyl)carbamoyl) acetamide (5j)" should
be -- 2-(benzo[d][1,3]dioxol-5-yloxy)-N-((4-bromo-3-methoxyphenyl)carbamoyl) acetamide (5j) --.

Column 18, Lines 43-44,
"2-(benzo[d][1,3]dioxo1-5-yloxy)-N-((4-phenoxyphenyl)carbamoyl)acetamide (5k)" should be
-- 2-(benzo[d][1,3]dioxol-5-yloxy)-N-((4-phenoxyphenyl)carbamoyl)acetamide (5k) --.

Column 19, Lines 9-10,
"2-(benzo[d][1,3]dioxo1-5-yloxy)-N-((4-methoxybenzyl)carbamoyl)acetamide (5l)" should be
-- 2-(benzo[d][1,3]dioxol-5-yloxy)-N-((4-methoxybenzyl)carbamoyl)acetamide (5l) --.

Column 19, Lines 40-41,
"N42-(1H-indol-3-yl)ethyl)carbamoyl)-2-(benzo[d][1,3]dioxo1-5-yloxy) acetamide (5m)" should be
-- N-((2-(1H-indol-3-yl)ethyl)carbamoyl)-2-(benzo[d][1,3]dioxol-5-yloxy) acetamide (5m) --.

Column 20, Lines 9-10,
"2-(benzo[d][1,3]dioxo1-5-yloxy)-N-((2,4-dimethoxyphenyl)carbamoyl) acetamide (5n)" should be
-- 2-(benzo[d][1,3]dioxol-5-yloxy)-N-((2,4-dimethoxyphenyl)carbamoyl) acetamide (5n) --.

Signed and Sealed this
Seventh Day of June, 2022

Katherine Kelly Vidal
*Director of the United States Patent and Trademark Office*

CERTIFICATE OF CORRECTION (continued)
U.S. Pat. No. 11,306,073 B2

Column 21, Lines 9-10,
"2-(benzo[d][1,3]dioxo1-5-yloxy)-N-((2-fluorophenyl)carbamoyl)acetamide (5p)" should be
-- 2-(benzo[d][1,3]dioxol-5-yloxy)-N-((2-fluorophenyl)carbamoyl)acetamide (5p) --.

Column 27, Lines 42-43,
"N-((2-(1H-indol-3-yl)ethyl)carbamoyl)-2-(3,5-bis(trifluoromethyl)phenoxyl acetamide (5ac)" should be -- N-((2-(1H-indol-3-yl)ethyl)carbamoyl)-2-(3,5-bis(trifluoromethyl)phenoxy) acetamide (5ac) --.

Column 31, Lines 25-26,
"2-(4-(benzyl oxy)phenoxy)-N-((2-fluorophenyl)carbamoyl)acetamide (5ak)" should be
-- 2-(4-(benzyloxy)phenoxy)-N-((2-fluorophenyl)carbamoyl)acetamide (5ak) --.